(12) United States Patent
Thaimattam et al.

(10) Patent No.: US 10,654,872 B1
(45) Date of Patent: May 19, 2020

(54) POLYMORPHS OF DOLUTEGRAVIR AND SALTS THEREOF

(71) Applicant: Laurus Labs Limited, Hyderabad (IN)

(72) Inventors: Ram Thaimattam, Hyderabad (IN); Rajesh Edupuganti, Hyderabad (IN); Venkata Sunil Kumar Indukuri, Hyderabad (IN); Srihari Raju Kalidindi, Hyderabad (IN); Satyanarayana Chava, Hyderabad (IN)

(73) Assignee: Laurus Labs Limited, Hyderabad (IN)

( * ) Notice: Subject to any disclaimer, the term of this patent is extended or adjusted under 35 U.S.C. 154(b) by 0 days.

(21) Appl. No.: 16/732,992

(22) Filed: Jan. 2, 2020

Related U.S. Application Data

(62) Division of application No. 15/750,595, filed as application No. PCT/IB2016/054974 on Aug. 19, 2016, now Pat. No. 10,597,404.

(30) Foreign Application Priority Data

Aug. 19, 2015 (IN) .......................... 4334/CHE/2015

(51) Int. Cl.
*C07D 498/14* (2006.01)
*A61K 31/5365* (2006.01)

(52) U.S. Cl.
CPC ........ *C07D 498/14* (2013.01); *A61K 31/5365* (2013.01); *C07B 2200/13* (2013.01)

(58) Field of Classification Search
CPC .................................................... C07D 498/14

USPC ....................................................... 514/230.2
See application file for complete search history.

(56) References Cited

U.S. PATENT DOCUMENTS 8,129,385 B2  3/2012  Johns et al.
10,087,193 B2  10/2018  Jetti et al.

FOREIGN PATENT DOCUMENTS

| WO | WO-2010068253 A1 | 6/2010 |
| WO | WO-2013038407 A1 | 3/2013 |
| WO | WO-2015092752 A1 | 6/2015 |
| WO | WO-2015118460 A1 | 8/2015 |
| WO | WO-2015138933 A1 | 9/2015 |
| WO | WO-2015139591 A1 | 9/2015 |
| WO | WO-2016016279 A1 | 2/2016 |
| WO | WO-2016102078 A1 | 6/2016 |

OTHER PUBLICATIONS

Crystalline form of sodium (4R,12aS)-9-{[(2,4-difluorophenyl)methyl]carbamoyl}-4-methyl-6,8-dioxo-3,4,6,8,12,12a-hexahydro-2H-pyrido[1',2':4,5]pyrazino[2,1-b][1,3]oxazin-7-olate; An IP.com Prior Art Database Technical Disclosure; IP.com No. IPCOM000238311D; IP.com Electronic Publication Date: Aug. 17, 2014.
International Search Report for PCT/IB2016/054974.

*Primary Examiner* — Kahsay Habte
(74) *Attorney, Agent, or Firm* — Blank Rome LLP

(57) ABSTRACT

The present invention relates to novel crystalline forms of dolutegravir, process for its preparation and pharmaceutical composition comprising them.

6 Claims, 26 Drawing Sheets

POLYMORPHS OF DOLUTEGRAVIR AND SALTS THEREOF

PRIORITY

This application is a divisional application of U.S. patent application Ser. No. 15/750,595, filed on Feb. 6, 2018, which is a national phase application that claims the benefit of International Application PCT/IB2016/054974, filed on 19 Aug. 2015, which is based on and claims the benefit of Indian Provisional Application No. 4334/CHE/2015, filed on Aug. 19, 2015, entitled "Novel Polymorphs of Dolutegravir and Salts Thereof", the contents of each of which are incorporated by reference herein.

FIELD OF THE INVENTION

The present invention relates to novel polymorphs of dolutegravir and salts thereof, process for their preparation and pharmaceutical composition comprising the same.

BACKGROUND OF THE INVENTION

Dolutegravir is chemically known as (4R,12aS)-9-{[(2,4-difluorophenyl)methyl]carbamoyl}-4-methyl-6,8-dioxo-3,4,6,8,12,12a-hexahydro-2H-pyrido[1',2':4,5]pyrazino [2,1-b][1,3]oxazin-7-olate and represented by the following structural formula;

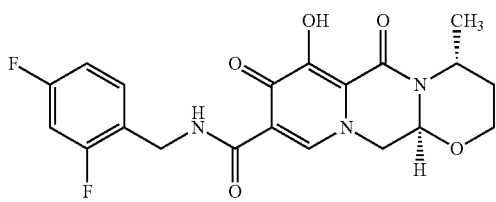 [SMILES: C[C@@H]1CCO[C@H]2Cn3cc(C(=O)NCc4ccc(F)cc4F)c(=O)c(O)c3C(=O)N12]

Dolutegravir (DTG, GSK1349572) is an integrase inhibitor being developed for the treatment of human immunodeficiency virus (HIV)-1 infection. Sodium salt of dolutegravir was recently approved by FDA and marketed under the brand name of TIVICAY by ViiV Healthcare and manufactured by GlaxoSmithKline. TIVICAY is administered orally as a tablet of 50 mg strength.

Tivicay is a human immunodeficiency virus type 1 (HIV-1) integrase strand transfer inhibitor (INSTI) indicated in combination with other antiretroviral agents for the treatment of HIV-1 infection.

Dolutegravir and process for its preparation were first described in U.S. Pat. No. 8,129,385. However this patent does not discloses any characteristic details of dolutegravir or its salts such as sodium.

WO2010068253 publication discloses anhydrous and monohydrate crystalline form of dolutegravir sodium characterized by PXRD and IR spectrum. Anhydrous dolutegravir sodium obtained by treating the solution of dolutegravir in ethanol with aqueous sodium hydroxide at 80° C.; whereas the monohydrate form was obtained by dissolving the anhydrous dolutegravir sodium in THF-water followed by treatment with aqueous sodium hydroxide. This publication further discloses the crystalline form of dolutegravir free acid along with its PXRD.

WO 2013038407 publication discloses amorphous form of dolutegravir sodium, process for its preparation and pharmaceutical composition comprising the same.

IP.com journal, ID No: IPCOM000238311D discloses the crystalline form of dolutegravir sodium characterized by PXRD, which is obtained by treating dolutegravir in tetrahydrofuran with aqueous sodium hydroxide at reflux temperature.

WO2015092752 publication discloses crystalline Form-M1 of dolutegravir sodium and process for its preparation.

WO2015118460 publication discloses crystalline Form-M2. Form-M3 and Form-M4 of dolutegravir sodium and process for their preparation.

WO2015138933 publication discloses crystalline Form-II, Form-III, Form-IV, Form-V, Form-VI, Form-VII, Form-VIII, Form-IX, Form-X and Form-XI of dolutegravir sodium, process for their preparation, pharmaceutical composition comprising them and uses thereof.

WO2015139591 publication discloses polymorphic Form-A, Form-B, Form-C, Form-D and Form-E of dolutegravir sodium and pharmaceutical composition comprising them.

WO2016016279 publication discloses crystalline Form-HxA, Form-Hy1B and Form-$S_{ETOH,H2O}$ of dolutegravir sodium, process for their preparation and pharmaceutical composition comprising them.

WO2016102078 publication discloses crystalline form of dolutegravir sodium 1,2-propylene glycol solvate, process for its preparation and pharmaceutical composition comprising the same.

Our co-pending IN application number 3105/CHE/2015 discloses crystalline form of dolutegravir sodium designated as Form-L1, Form-L2, Form-L3, Form-L4, Form-L5, Form-L6, Form-L7 and Form-L8, amorphous form of dolutegravir, solid dispersion of dolutegravir sodium with one or more pharmaceutically acceptable excipient and crystalline benzyltrimethyl ammonium salt of dolutegravir.

Polymorphism is the occurrence of different crystalline forms of a single compound and it is a property of some compounds and complexes. Thus, polymorphs are distinct solids sharing the same molecular formula, yet each polymorph may have distinct physical properties. Therefore, a single compound may give rise to a variety of polymorphic forms where each form has different and distinct physical properties, such as different solubility profiles, different melting point temperatures and/or different x-ray diffraction peaks. Since the solubility of each polymorph may vary, identifying the existence of pharmaceutical polymorphs is essential for providing pharmaceuticals with predictable solubility profiles. It is desirable to investigate all solid state forms of a drug, including all polymorphic forms and solvates, and to determine the stability, dissolution and flow properties of each polymorphic form.

Dolutegravir is one of the important drugs available in the market for the treatment of human immunodeficiency virus (HIV)-1 infection. Hence it's important to discover new polymorphic forms of dolutegravir and its salt, which may provide a new opportunity to improve the performance characteristics of a pharmaceutical product. Hence the main object of the present invention is to provide novel polymorphic forms of dolutegravir and salts thereof, especially sodium.

SUMMARY OF THE INVENTION

The present invention provides novel polymorphic forms of dolutegravir and salts thereof, especially sodium, process for their preparation and pharmaceutical compositions comprising one or more of the novel polymorphic forms of dolutegravir and its salts. The polymorphic forms of dolutegravir sodium of the present invention have advantageous properties selected from at least one of: chemical purity, flowability, solubility, morphology or crystal habit, stability—such as storage stability, stability to dehydration, and stability to polymorphic conversion, low hygroscopicity, and low content of residual solvents.

In one embodiment, the present invention provides novel polymorphic forms of dolutegravir sodium; which are designated herein as dolutegravir sodium Form-L9, dolutegravir sodium Form-L10, dolutegravir sodium Form-L11 and dolutegravir sodium Form-L12.

In another embodiment the present invention provides a process for the preparation of novel polymorphic forms of dolutegravir sodium Form-L9, Form-L10, Form-L11 and Form-L12 and other crystalline forms of dolutegravir sodium.

In another embodiment, the present invention provides novel solvates of dolutegravir such as morpholine solvate and 1-amino-2-propanol solvate.

In another embodiment, the present invention provides polymorphic forms of morpholine and 1-amino-2-propanol solvate of dolutegravir as well as process for their preparation.

In another embodiment, the present invention provides a pharmaceutical composition comprising the novel polymorphic forms of dolutegravir and salts thereof described above and at least one pharmaceutically acceptable excipient.

BRIEF DESCRIPTION OF THE DRAWINGS

The accompanying drawings, which are incorporated in and constitute a part of this specification, illustrate several embodiments of the invention and together with the description, serve to explain the principles of the invention.

DETAILED DESCRIPTION OF THE INVENTION

The present invention provides novel polymorphic forms of dolutegravir and salts thereof, process for their preparation and pharmaceutical compositions comprising one or more of such polymorphic forms.

The polymorphic forms of dolutegravir sodium and dolutegravir of the present invention are characterized by one or more analytical methods such as X-ray powder diffraction (XRPD) patterns, Differential scanning calorimetry (DSC) and Thermo gravimetric analysis (TGA).

In one embodiment, the present invention provides novel polymorphic forms of dolutegravir sodium, which are designated as dolutegravir sodium Form-L9, dolutegravir sodium Form-L10, dolutegravir sodium Form-L11 and dolutegravir sodium Form-L12.

In another embodiment, the present invention provides dolutegravir sodium Form-L9.

Figure 1:
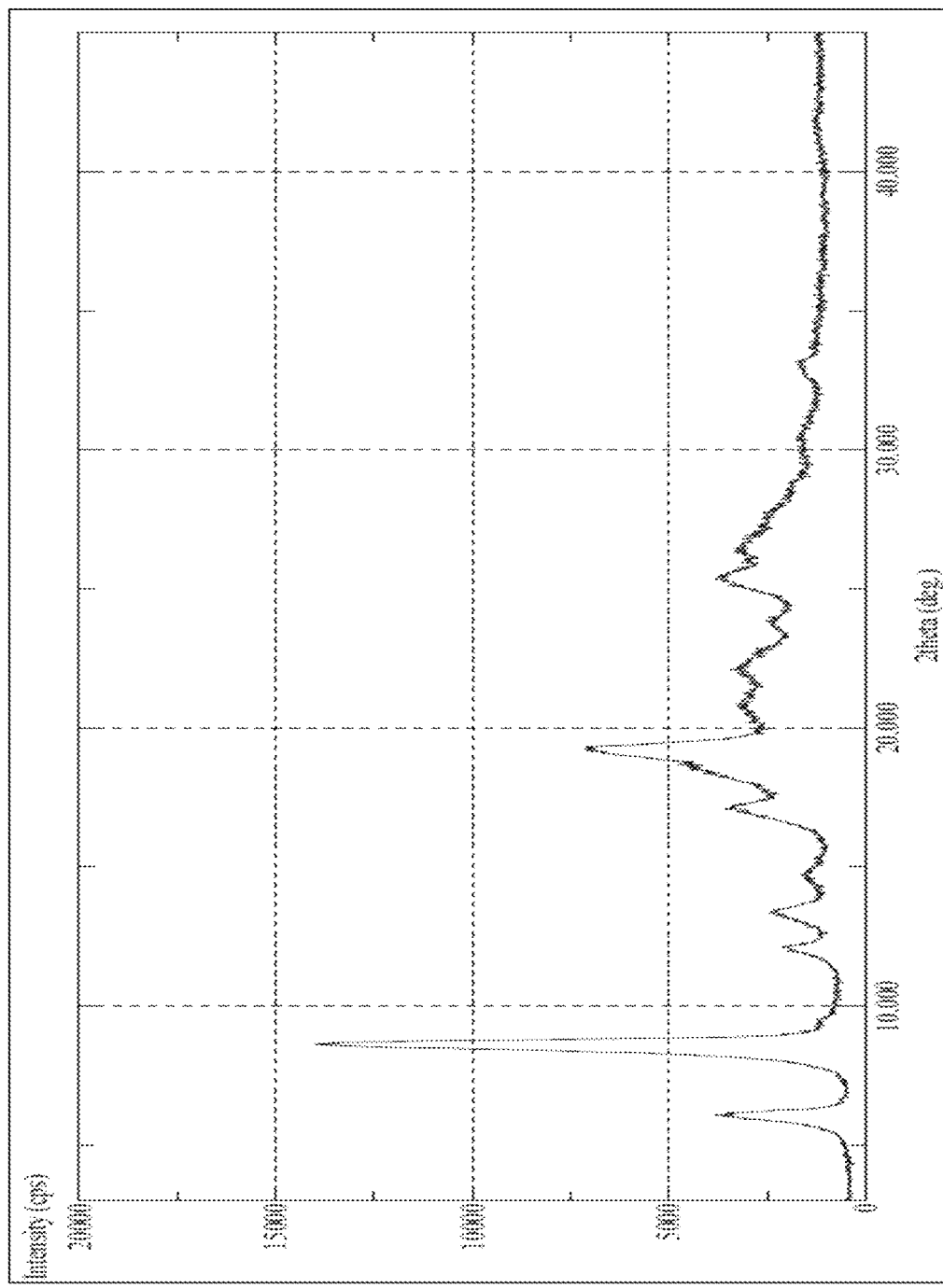
FIG. 1 is the characteristic powder X-ray diffraction (XRD) pattern of dolutegravir sodium Form-L9.

In another embodiment, the present invention provides dolutegravir sodium Form-L9, characterized by a powder X-Ray diffraction (PXRD) pattern substantially in accordance with FIG. 1.

In another embodiment, the present invention provides dolutegravir sodium Form-L9 characterized by a powder X-Ray diffraction pattern having one or more peaks at about 6.1, 8.6, 12.1, 13.4, 17.1, 18.6, 19.3, 22.4, 23.8, 25.4 and 26.3±0.2° 2θ.

Figure 2:
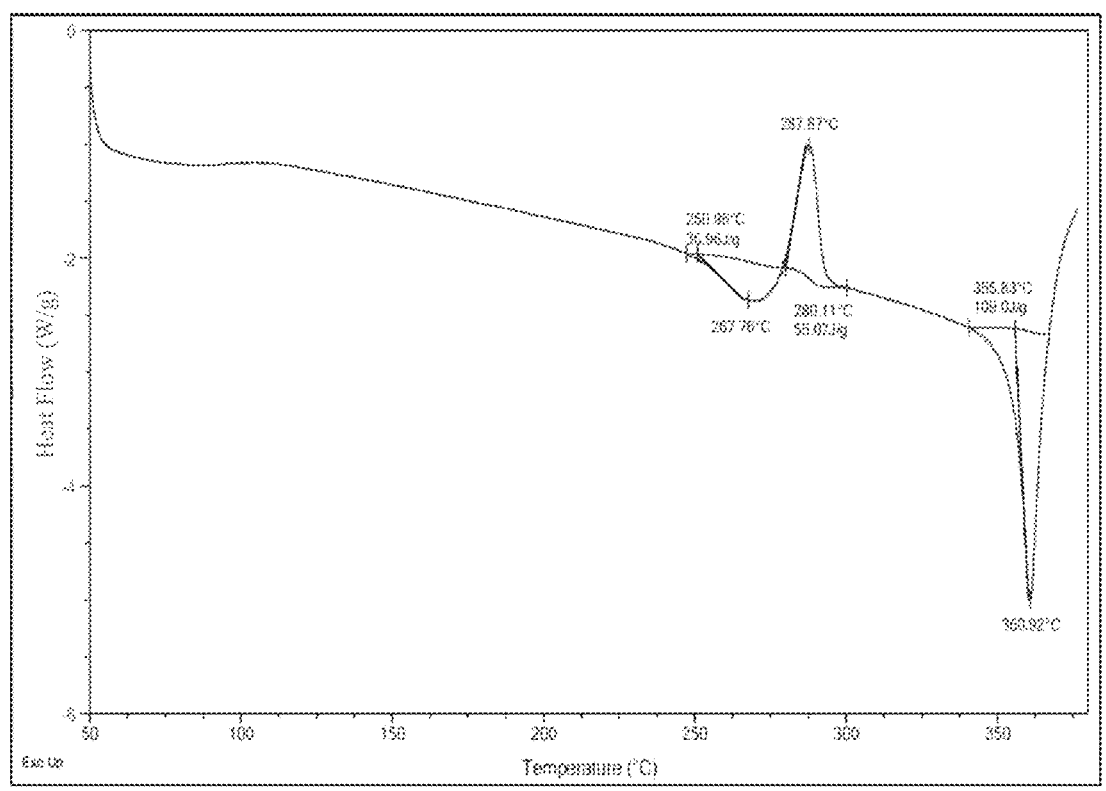
FIG. 2 is the characteristic differential scanning calorimetric (DSC) thermogram of dolutegravir sodium Form-L9.

In another embodiment, the present invention provides dolutegravir sodium Form-L9, characterized by a differential scanning calorimetry (DSC) substantially in accordance with FIG. 2.

Figure 3:
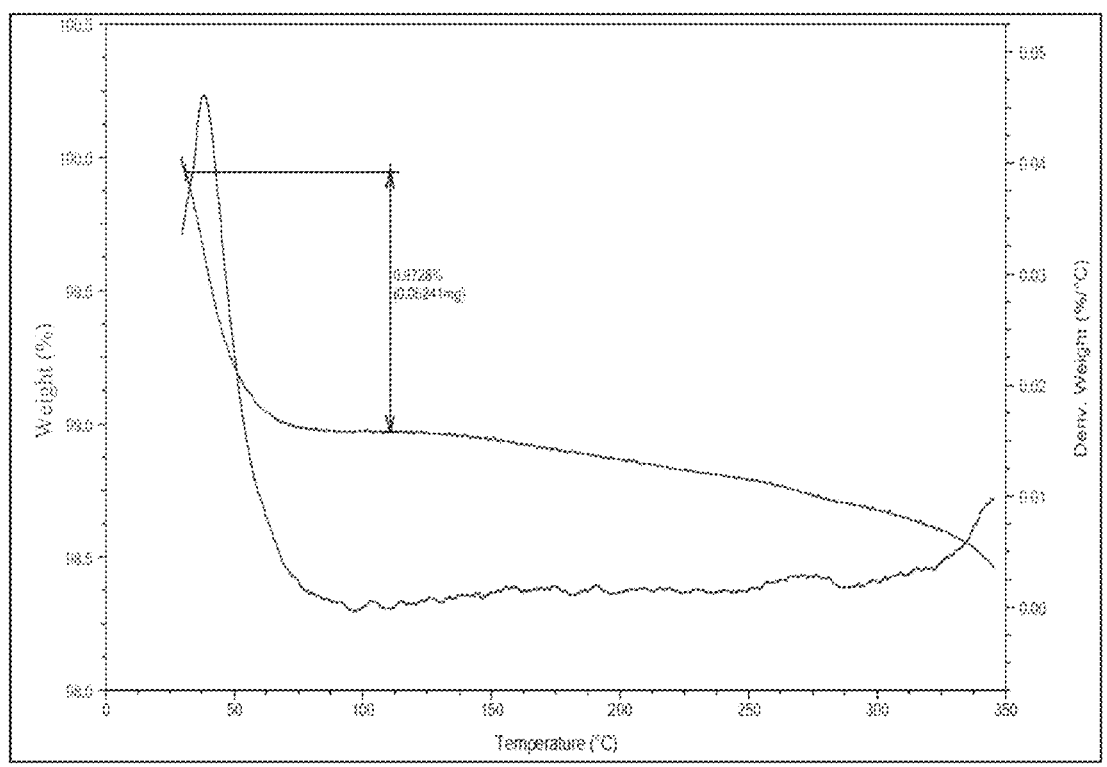
FIG. 3 is the characteristic thermo gravimetric analysis (TGA) of dolutegravir sodium Form-L9.

In another embodiment, the present invention provides dolutegravir sodium Form-L9, characterized by a thermo gravimetric analysis (TGA) substantially in accordance with FIG. 3.

In another embodiment, the present invention provides dolutegravir sodium Form-L9, characterized by a powder X-Ray diffraction (PXRD) pattern substantially in accordance with FIG. 1, a differential scanning calorimetry (DSC) substantially in accordance with FIG. 2, and/or a thermo gravimetric analysis (TGA) substantially in accordance with FIG. 3.

In another embodiment, the present invention provides a process for preparation of dolutegravir sodium Form-L9, which comprise of de-solvating dolutegravir sodium 1-pentanol solvate (Form-L12, characterized by a powder X-Ray diffraction pattern having one or more peaks at about 5.32, 7.50, 9.16, 11.46, 12.98, 13.72, 15.02, 15.84, 16.42, 18.60, 19.58, 20.08, 20.50, 21.00, 21.98, 23.06, 23.90, 24.46, 25.78, 26.28, 27.18 and 28.36±0.2° 2θ) by heating at a suitable temperature of about 110° C. to about 135° C., preferably at about 120° C. to about 125° C. for a sufficient period of time, preferably for 4 hrs to 12 hrs under vacuum to provide dolutegravir sodium Form-L9.

In another embodiment, the present invention provides a process for the preparation of Form-L9, which comprise of
a) suspending or mixing dolutegravir in 1-pentanol,
b) adding sodium hydroxide to step a) at a suitable temperature,
c) stirring the reaction mass at a suitable temperature,
d) isolating the dolutegravir sodium and drying the wet solid at a suitable temperature, and
e) exposing the dried compound under atmosphere air or humid air to obtain dolutegravir sodium Form-L9.

In step a) of the aforementioned process involves suspending or mixing dolutegravir in 1-pentanol. The step of suspending or mixing dolutegravir in 1-pentanol can be carried out by adding dolutegravir to 1-pentanol at a suitable temperature of about 25° C. to about 45° C., preferably at about 25° C. to about 35° C. Then, sodium hydroxide is added to form dolutegravir sodium salt. The addition of sodium hydroxide is carried out at a temperature of about 25° C. to about 45° C., preferably at about 25° C. to about 35° C. The sodium hydroxide may be taken as in the form of solid or as an aqueous solution or as a solvent containing solution; preferably aqueous sodium hydroxide solution is used.

The step c) of stirring the reaction mass is carried out for a sufficient period of time at about 25° C. to about 45° C. Then, the precipitated solid dolutegravir sodium can be separated by filtration. The obtained solid dolutegravir sodium may be dried at about 25° C. to about 120° C. for sufficient period of time under atmospheric pressure or under reduced pressure, until traces of I-pentanol solvent substantially removed. For example, the wet dolutegravir sodium can be dried initially at 25-35° C., further at 50-55° C. and finally at 100-110° C. under vacuum.

The step e) of exposing dolutegravir sodium of step d) under atmosphere air or humid air can be carried out by keeping the compound in atmospheric air chambers or in a humidity chambers at a temperature of about 25° C. to about 35° C. for a sufficient period of about 2 hrs to 36 hrs, preferably for about 4 hrs to 16 hrs, more preferably for about 6 hrs to obtain dolutegravir sodium Form-L9.

In another embodiment, the present invention provides dolutegravir sodium Form-L10.

In another embodiment, the dolutegravir sodium Form-L10 of the present invention is an isopentanol solvate.

Figure 4:
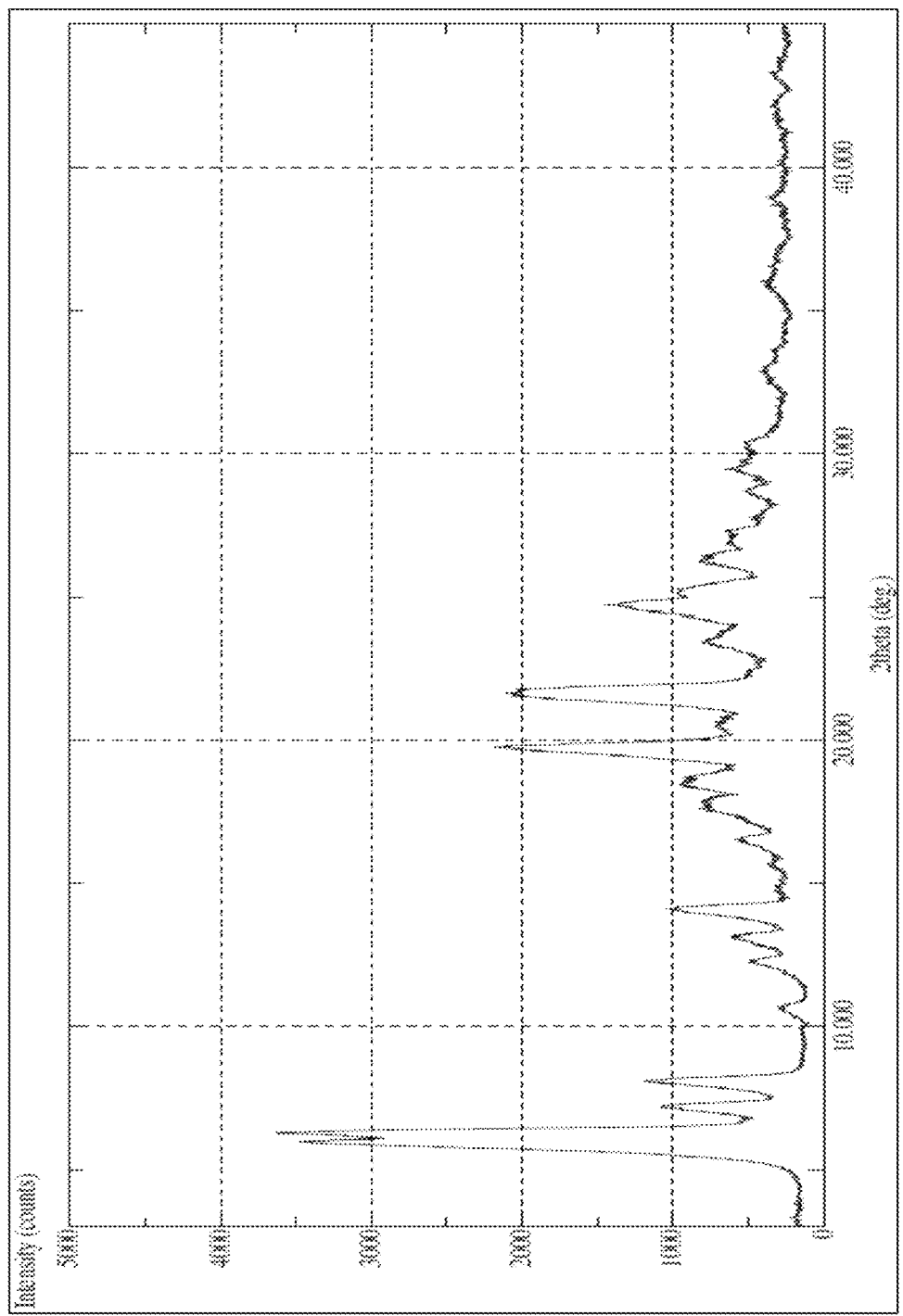
FIG. 4 is the characteristic powder X-ray diffraction (XRD) pattern of dolutegravir sodium Form-L10.

In another embodiment, the present invention provides dolutegravir sodium Form-L10, characterized by a powder X-Ray diffraction (PXRD) pattern substantially in accordance with FIG. 4.

In another embodiment, the present invention provides dolutegravir sodium Form-L10 characterized by a powder X-Ray diffraction pattern having one or more peaks at about 5.94, 6.30, 7.22, 8.10, 10.58, 12.20, 13.08, 14.12, 15.74, 16.48, 17.88, 18.40, 19.74, 21.72, 23.40, 24.72, 25.24, 26.44, 27.02, 28.60 and 29.54±0.2° 2θ.

Figure 5:
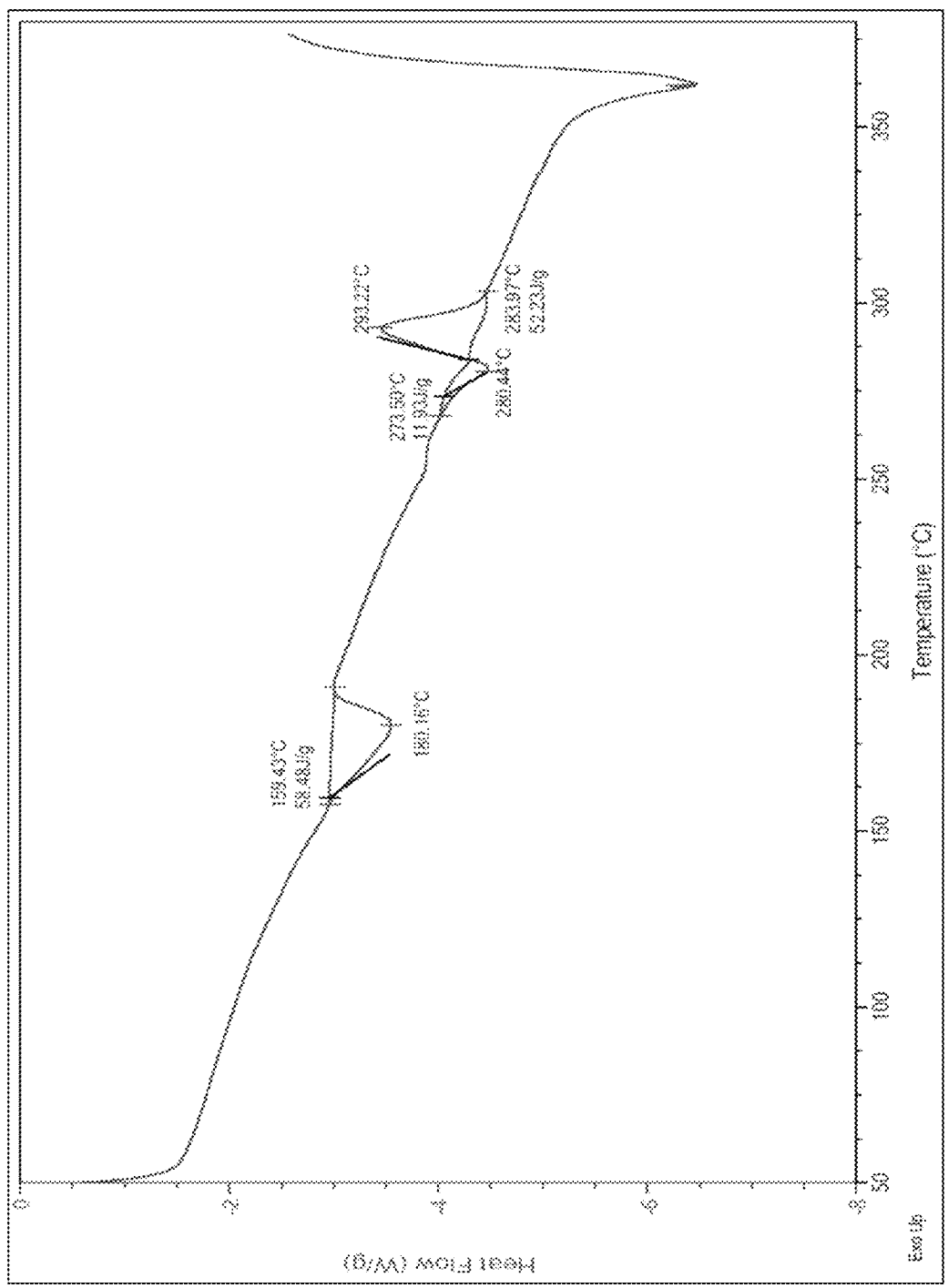
FIG. 5 is the characteristic differential scanning calorimetric (DSC) thermogram of dolutegravir sodium Form-L10.

In another embodiment, the present invention provides dolutegravir sodium Form-L10, characterized by a differential scanning calorimetry (DSC) substantially in accordance with FIG. 5.

Figure 6:
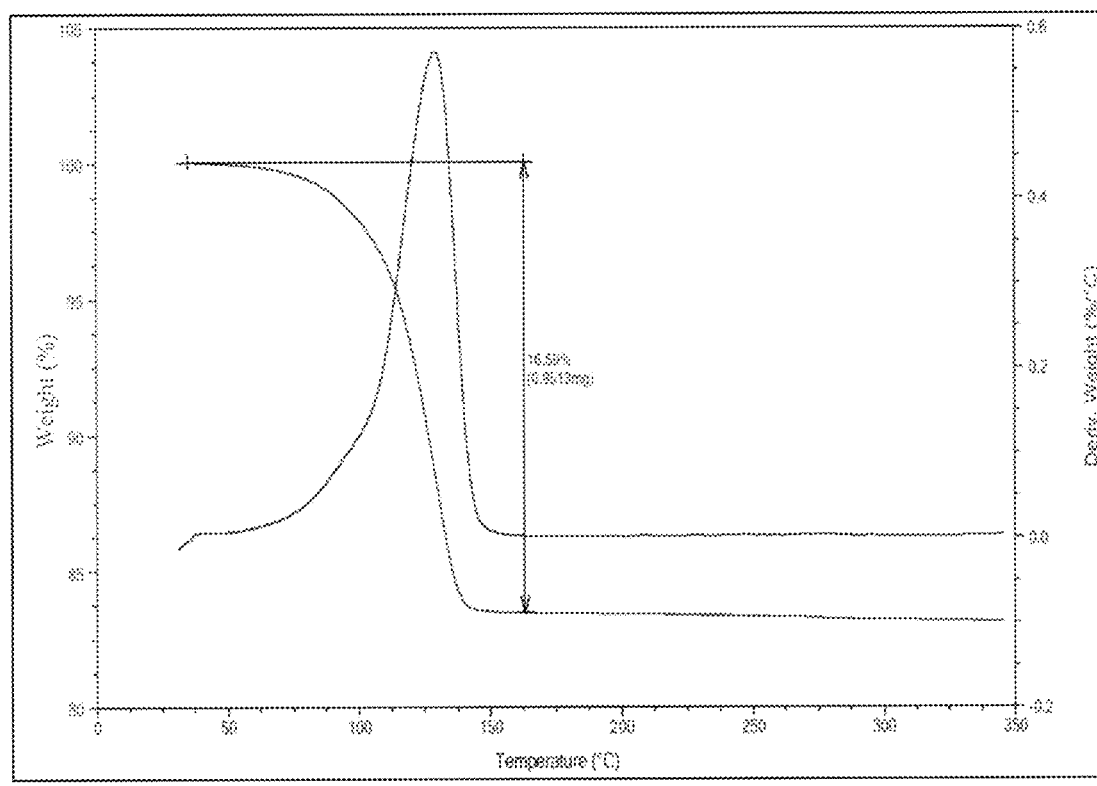
FIG. 6 is the characteristic thermo gravimetric analysis (TGA) of dolutegravir sodium Form-L10.

In another embodiment, the present invention provides dolutegravir sodium Form-L10, characterized by a thermo gravimetric analysis (TGA) substantially in accordance with FIG. 6.

In another embodiment, the present invention provides dolutegravir sodium Form-L10, characterized by a powder X-Ray diffraction (PXRD) pattern substantially in accordance with FIG. 4, a differential scanning calorimetry (DSC) substantially in accordance with FIG. 5 and/or a thermo gravimetric analysis (TGA) substantially in accordance with FIG. 6.

In another embodiment, the present invention provides a process for preparation of dolutegravir sodium Form-L10, which comprise of
a) suspending or mixing dolutegravir in isopentanol or its aqueous solution,
b) adding sodium hydroxide to step a) at a suitable temperature, and
c) isolating the dolutegravir sodium Form-L10.

In the aforementioned process of dolutegravir sodium Form-L10, suspending or mixing dolutegravir in isopentanol or its aqueous solution, preferably in aqueous isopentanol is carried out at a suitable temperature of about 25° C. to about 45° C., preferably at about 25° C. to about 35° C. Addition of sodium hydroxide of step b) can be used directly as a solid or as aqueous solution; preferably as an aqueous solution and added to step a) suspension at a suitable temperature of about 25° C. to about 45° C., preferably at about 25° C. to about 35° C. and stirred for a sufficient period of time, preferably for 2 hrs to 10 hrs. Then the isolation of dolutegravir sodium Form-L10 from the reaction mass can be carried out by any conventional techniques known in the art, for example filtration and followed by drying.

In another embodiment, the present invention provides dolutegravir sodium Form-L11.

In another embodiment, dolutegravir sodium Form-L11 of the present invention may be an isobutanol solvate.

Figure 7:
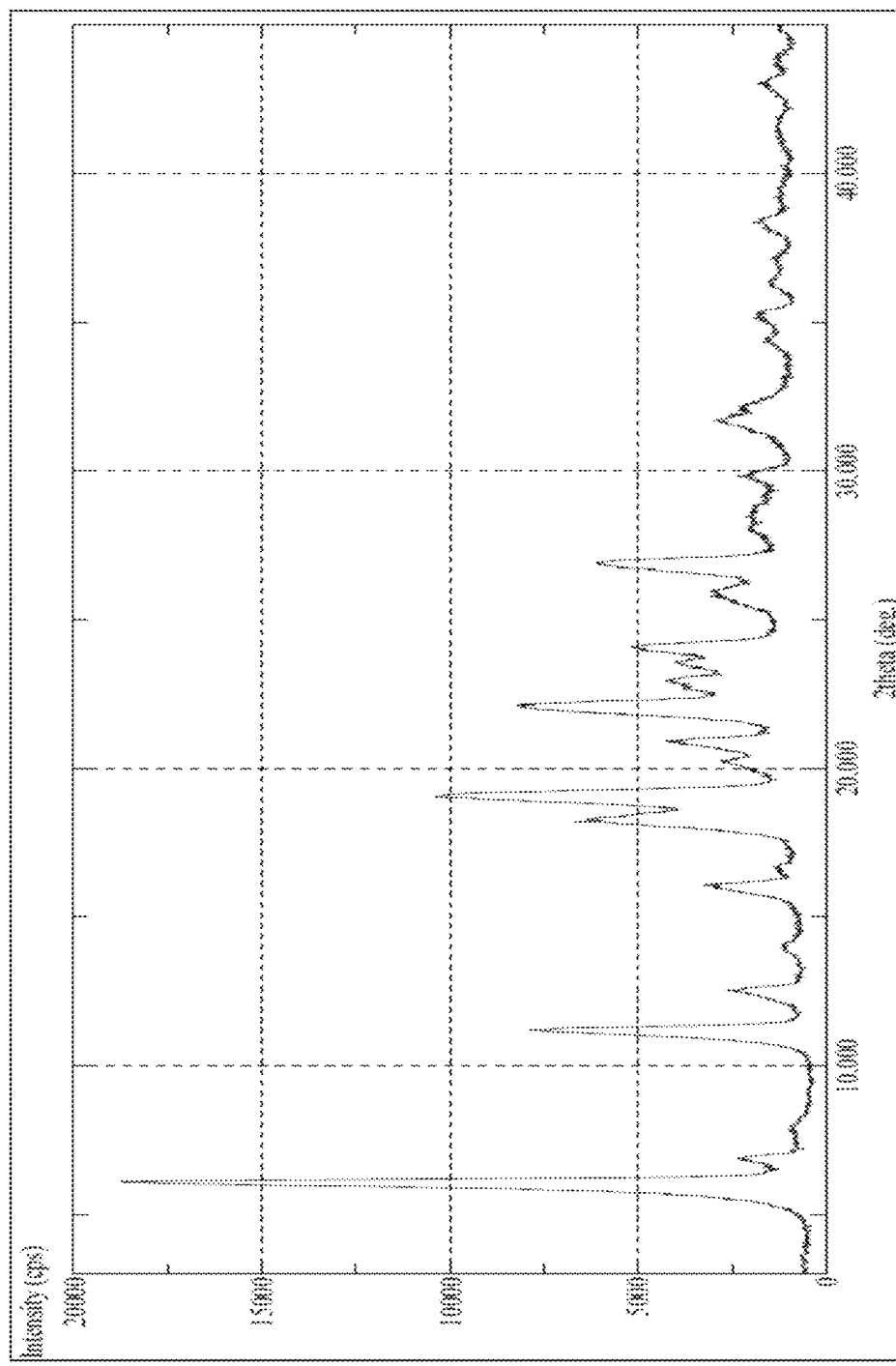
FIG. 7 is the characteristic powder X-ray diffraction (XRD) pattern of dolutegravir sodium Form-L11.

In another embodiment, the present invention provides dolutegravir sodium Form-L11, characterized by a powder X-Ray diffraction (PXRD) pattern substantially in accordance with FIG. 7.

In another embodiment, the present invention provides dolutegravir sodium Form-L11, characterized by a powder X-Ray diffraction pattern having one or more peaks at about 6.08, 6.92, 11.20, 12.48, 14.00, 16.04, 18.24, 19.08, 20.20, 20.90, 22.12, 22.70, 22.96, 23.54, 24.08, 25.84, 26.92, 29.84 and 31.68±0.2° 2θ.

Figure 8:
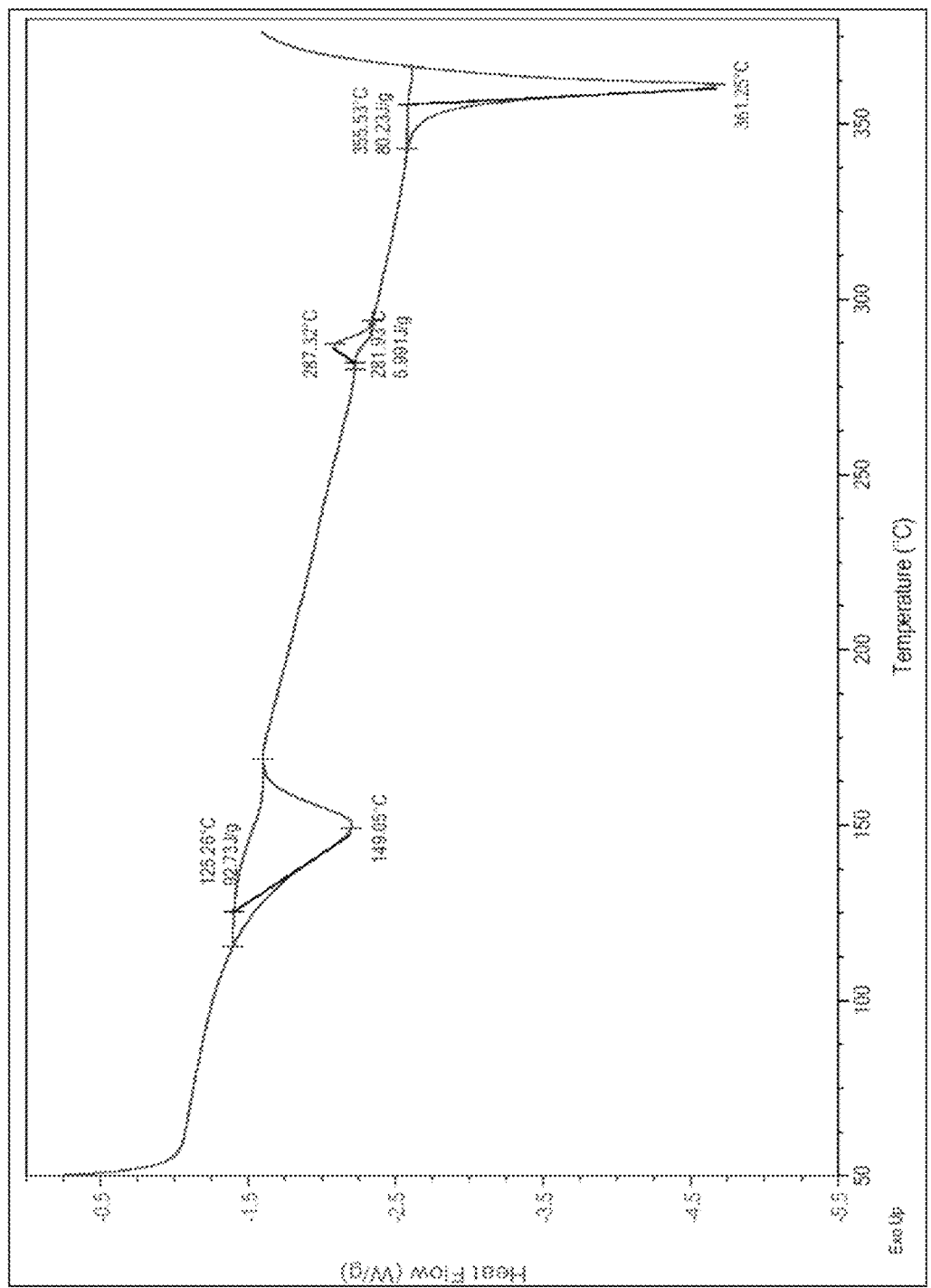
FIG. 8 is the characteristic differential scanning calorimetric (DSC) thermogram of dolutegravir sodium Form-L11.

In another embodiment, the present invention provides dolutegravir sodium Form-L11, characterized by a differential scanning calorimetry (DSC) substantially in accordance with FIG. 8.

Figure 9:
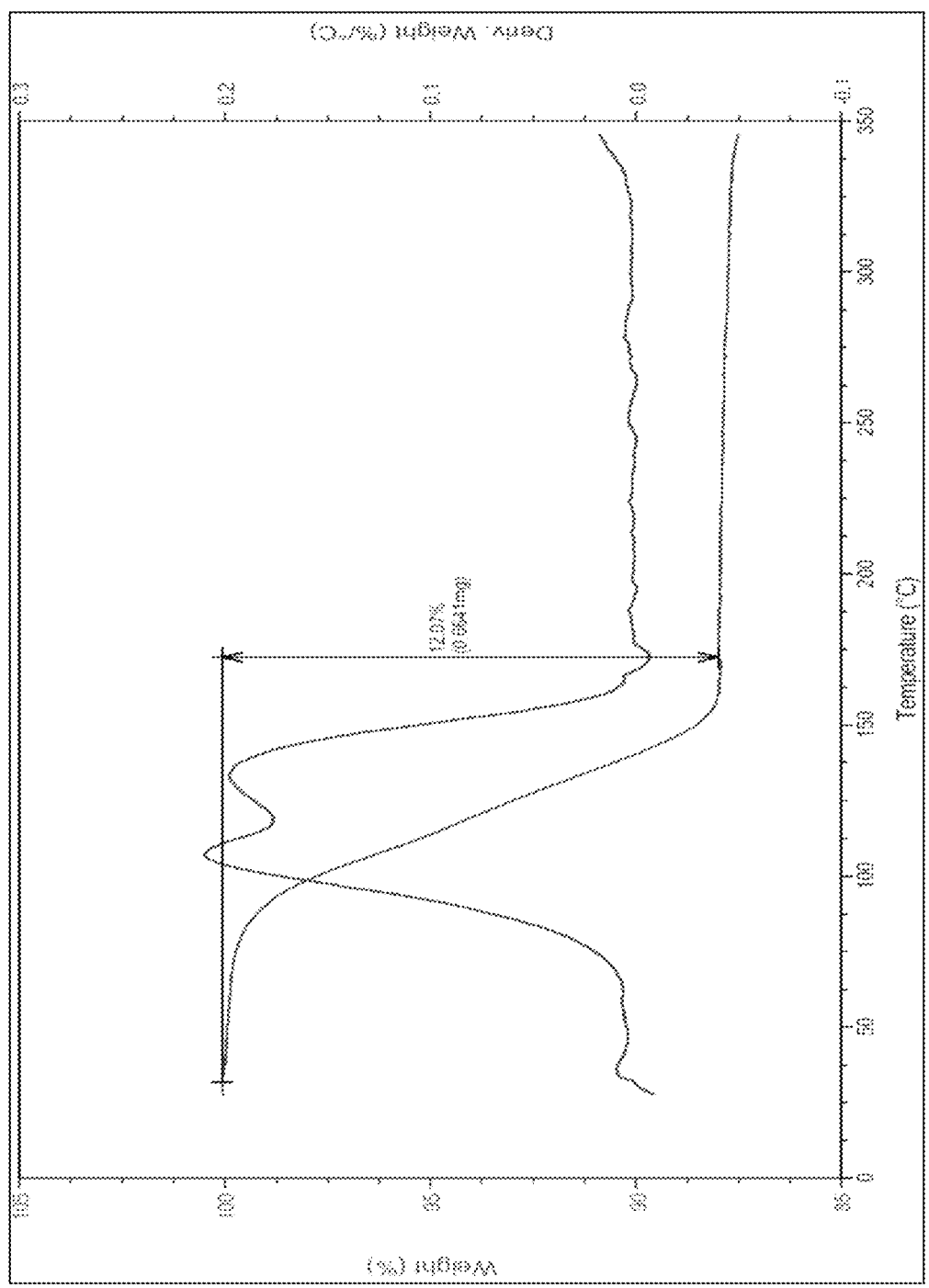
FIG. 9 is the characteristic thermo gravimetric analysis (TGA) of dolutegravir sodium Form-L11.

In another embodiment, the present invention provides dolutegravir sodium Form-L11, characterized by a thermo gravimetric analysis (TGA) substantially in accordance with FIG. 9.

In another embodiment, the present invention provides dolutegravir sodium Form-L11, characterized by a powder X-Ray diffraction (PXRD) pattern substantially in accordance with FIG. 7, a differential scanning calorimetry (DSC) substantially in accordance with FIG. 8 and/or a thermo gravimetric analysis (TGA) substantially in accordance with FIG. 9.

In another embodiment, the present invention provides a process for preparation of dolutegravir sodium Form-L11, which comprise of a) suspending or mixing dolutegravir in isobutanol or its aqueous solution,
b) adding sodium hydroxide to step a) at a suitable temperature,
c) optionally heating the suspension, and
d) isolating dolutegravir sodium Form-L11.

In the aforementioned process of dolutegravir sodium Form-L11, suspending or mixing dolutegravir in isobutanol or its aqueous solution, preferably in isobutanol can be carried out at a suitable temperature of about 25° C. to about 45° C., preferably at about 25° C. to about 35° C. In step b) sodium hydroxide can be used directly as a solid or as aqueous solution, preferably as aqueous sodium hydroxide solution and added to step a) suspension at a suitable temperature of about 25° C. to about 45° C., preferably at about 25° C. to about 35° C. and stirred for a sufficient period of time, preferably for 2 hrs to 20 hrs. Then the isolation of dolutegravir sodium Form-L11 from the reaction mass can be carried out by any conventional techniques known in the art, for example filtration and followed by drying.

In forgoing process, if heating the suspension in step c) is involved, then the reaction mass is heated to about 40° C. to about 70° C., preferably about 60° C. to about 65° C. and stirred for a sufficient period of time, preferably for 30 mins to 4 hrs. Then isolation of dolutegravir sodium Form-L11 can be carried out by any conventional techniques known in the art, for example cooling the reaction mass to about 25° C. to about 35° C., stirring followed by filtration and drying.

In another embodiment, the present invention provides dolutegravir sodium Form-L12.

In another embodiment, dolutegravir sodium Form-L12 of the present invention is a 1-pentanol solvate.

Figure 10:
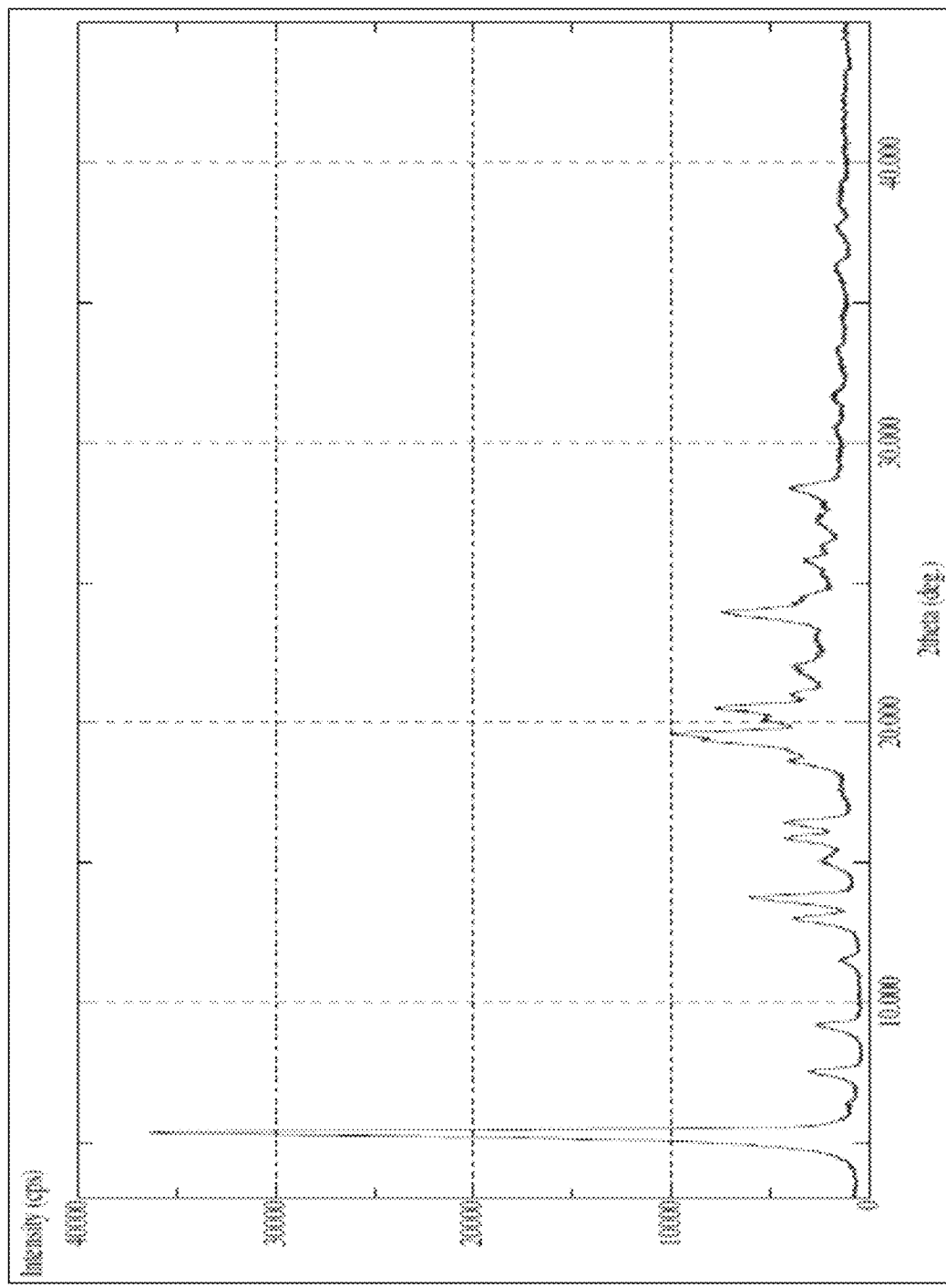
FIG. 10 is the characteristic powder X-ray diffraction (XRD) pattern of dolutegravir sodium Form-L12.

In another embodiment, the present invention provides dolutegravir sodium Form-L12, characterized by a powder X-Ray diffraction (PXRD) pattern substantially in accordance with FIG. 10.

In another embodiment, the present invention provides dolutegravir sodium Form-L12 characterized by a powder X-Ray diffraction pattern having one or more peaks at about 5.32, 7.50, 9.16, 11.46, 12.98, 13.72, 15.02, 15.84, 16.42, 18.60, 19.58, 20.08, 20.50, 21.00, 21.98, 23.06, 23.90, 24.46, 25.78, 26.28, 27.18 and 28.36±0.2° 2θ.

Figure 11:
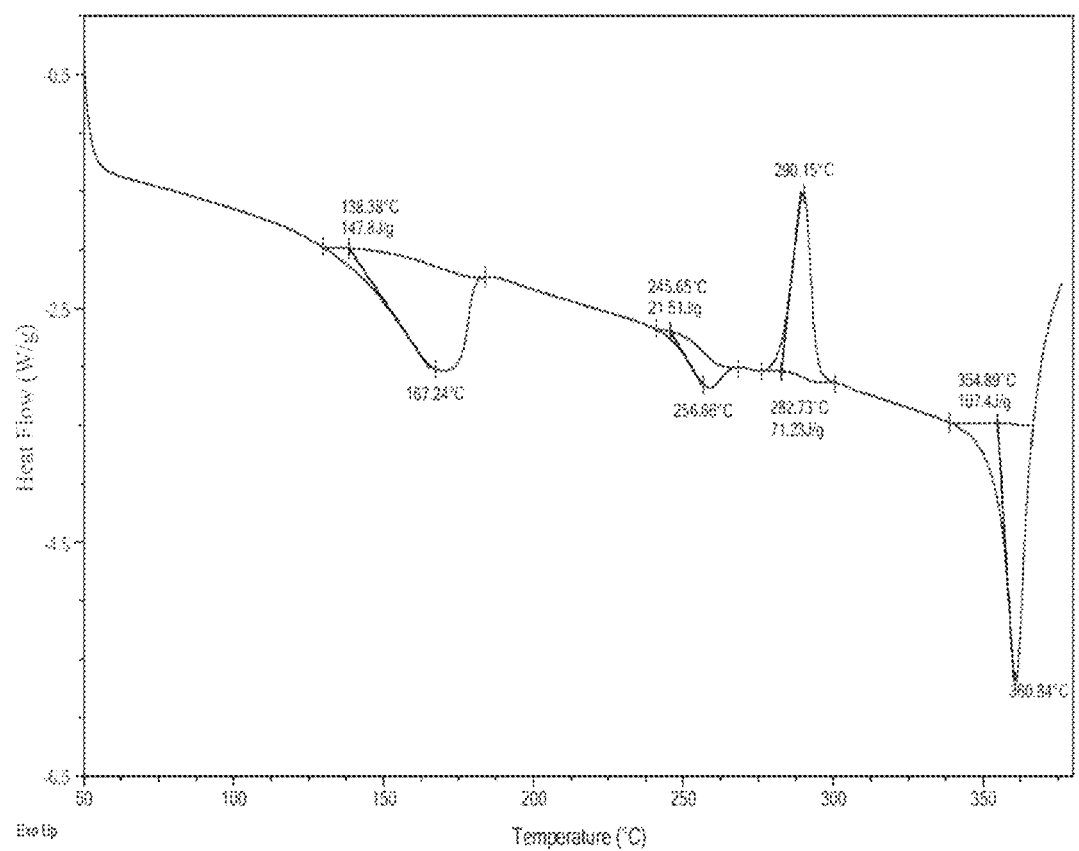
FIG. 11 is the characteristic differential scanning calorimetric (DSC) thermogram of dolutegravir sodium Form-L12.

In another embodiment, the present invention provides dolutegravir sodium Form-L12, characterized by a differential scanning calorimetry (DSC) substantially in accordance with FIG. 11.

Figure 12:
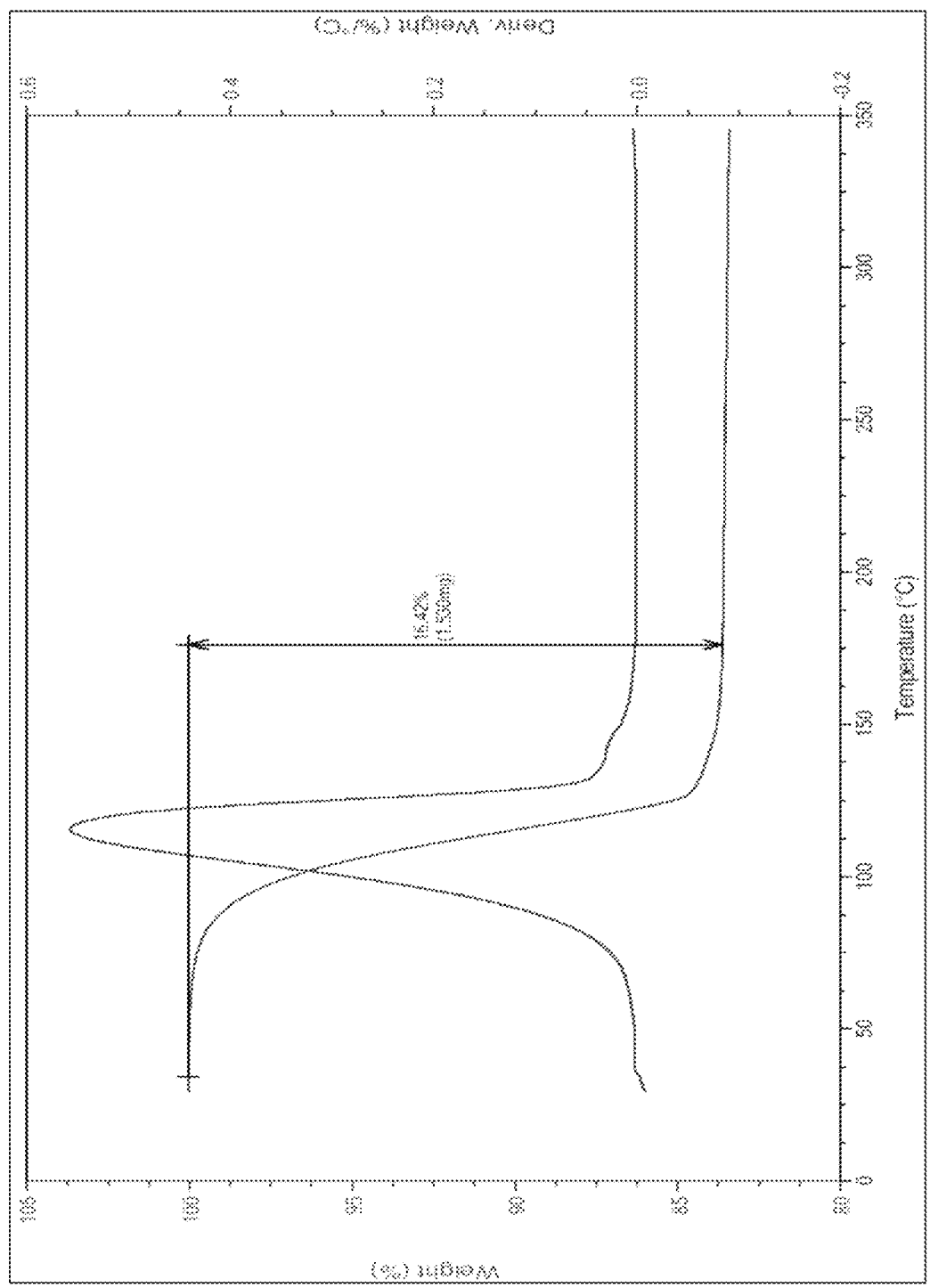
FIG. 12 is the characteristic thermo gravimetric analysis (TGA) of dolutegravir sodium Form-L12.

In another embodiment, the present invention provides dolutegravir sodium Form-L12, characterized by a thermo gravimetric analysis (TGA) substantially in accordance with FIG. 12.

In another embodiment, the present invention provides dolutegravir sodium Form-L12, characterized by a powder X-Ray diffraction (PXRD) pattern substantially in accordance with FIG. 10, a differential scanning calorimetry (DSC) substantially in accordance with FIG. 11 and/or a thermo gravimetric analysis (TGA) substantially in accordance with FIG. 12.

In another embodiment, the present invention provides a process for preparation of dolutegravir sodium Form-L12, which comprise of a) suspending or mixing dolutegravir in 1-pentanol or its aqueous solution,
b) adding sodium hydroxide to step a) at a suitable temperature, and
c) isolating dolutegravir sodium Form-L12.

In the aforementioned process of dolutegravir sodium Form-L12, suspending or mixing dolutegravir in 1-pentanol or its aqueous solution can be carried out at a suitable temperature of about 25° C. to about 45° C., preferably at about 25° C. to about 35° C. In step b) sodium hydroxide can be used directly as a solid or as aqueous solution; preferably as aqueous solution and added to step a) suspension at a suitable temperature of about 25° C. to about 45° C., preferably at about 25° C. to about 35° C. and stirred for a sufficient period of time, preferably for 2 hrs to 10 hrs. Then the isolation of dolutegravir sodium Form-L12 from the reaction mass can be carried out by any conventional techniques known in the art, for example filtration and followed by drying.

Figure 22:
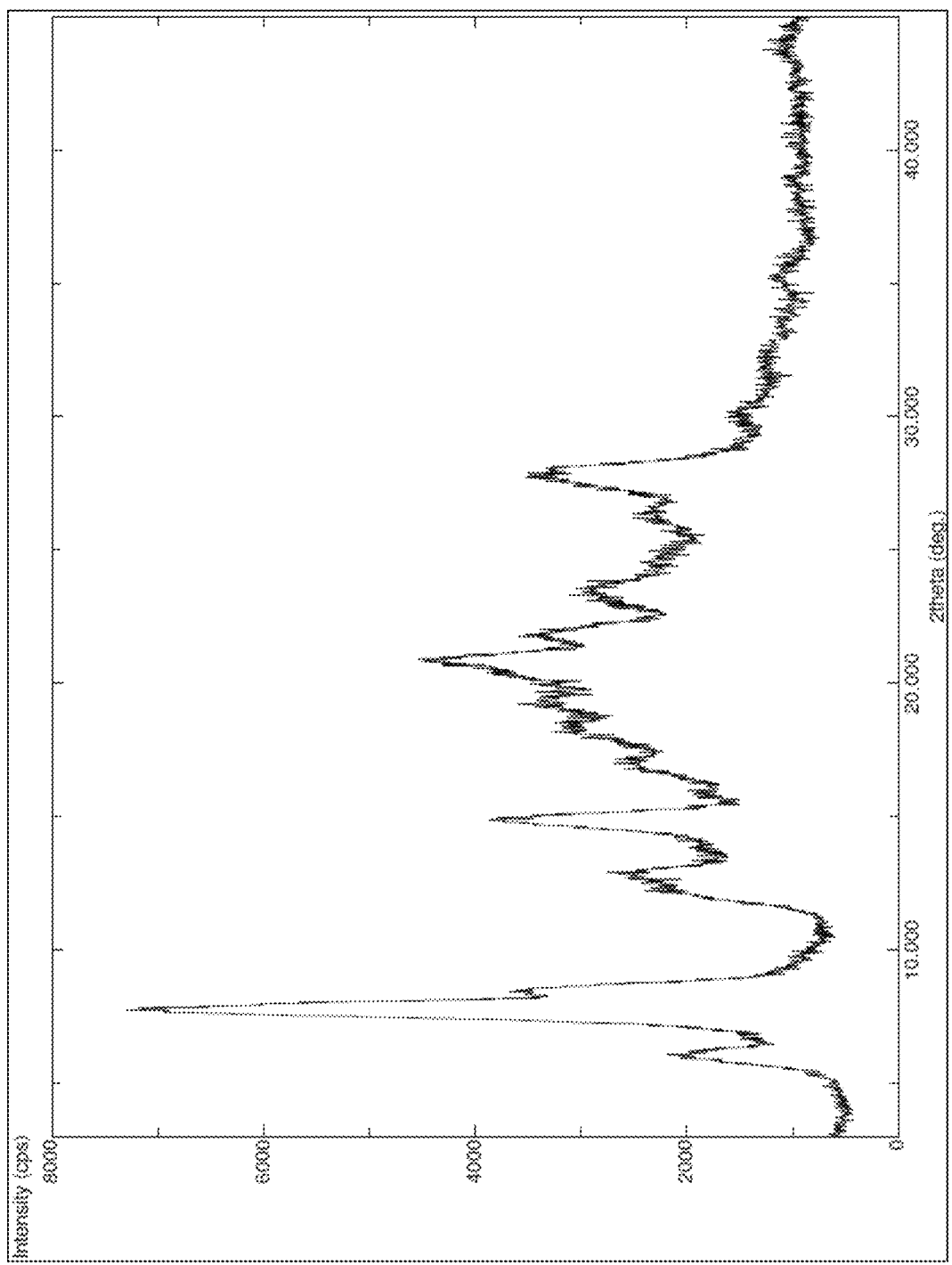
FIG. 22 is the characteristic powder X-ray diffraction (XRD) pattern of crystalline dolutegravir sodium obtained as per example-10.

In another embodiment, the present invention provides a process for preparation of crystalline dolutegravir sodium characterized by a powder X-Ray diffraction pattern having one or more peaks at about 5.98, 7.76, 8.52, 12.88, 14.88, 15.90, 16.84, 18.26, 19.20, 20.40, 20.86, 21.80, 23.44, 26.24, 27.72 and 30.16±0.2° 2θ or characterized by a powder X-Ray diffraction (PXRD) pattern substantially in accordance with FIG. 22, which comprise of: de-solvating dolutegravir sodium isopentanol solvate (Form-L10, characterized by a powder X-Ray diffraction pattern having one or more peaks at about 5.94, 6.30, 7.22, 8.10, 10.58, 12.20, 13.08, 14.12, 15.74, 16.48, 17.88, 18.40, 19.74, 21.72, 23.40, 24.72, 25.24, 26.44, 27.02, 28.60 and 29.54±0.2° 2θ) by heating at a suitable temperature of about 110° C. to about 135° C., preferably at about 120° C. to about 125° C. for a sufficient period of time, preferably for 4 hrs to 12 hrs under vacuum.

Figure 23:
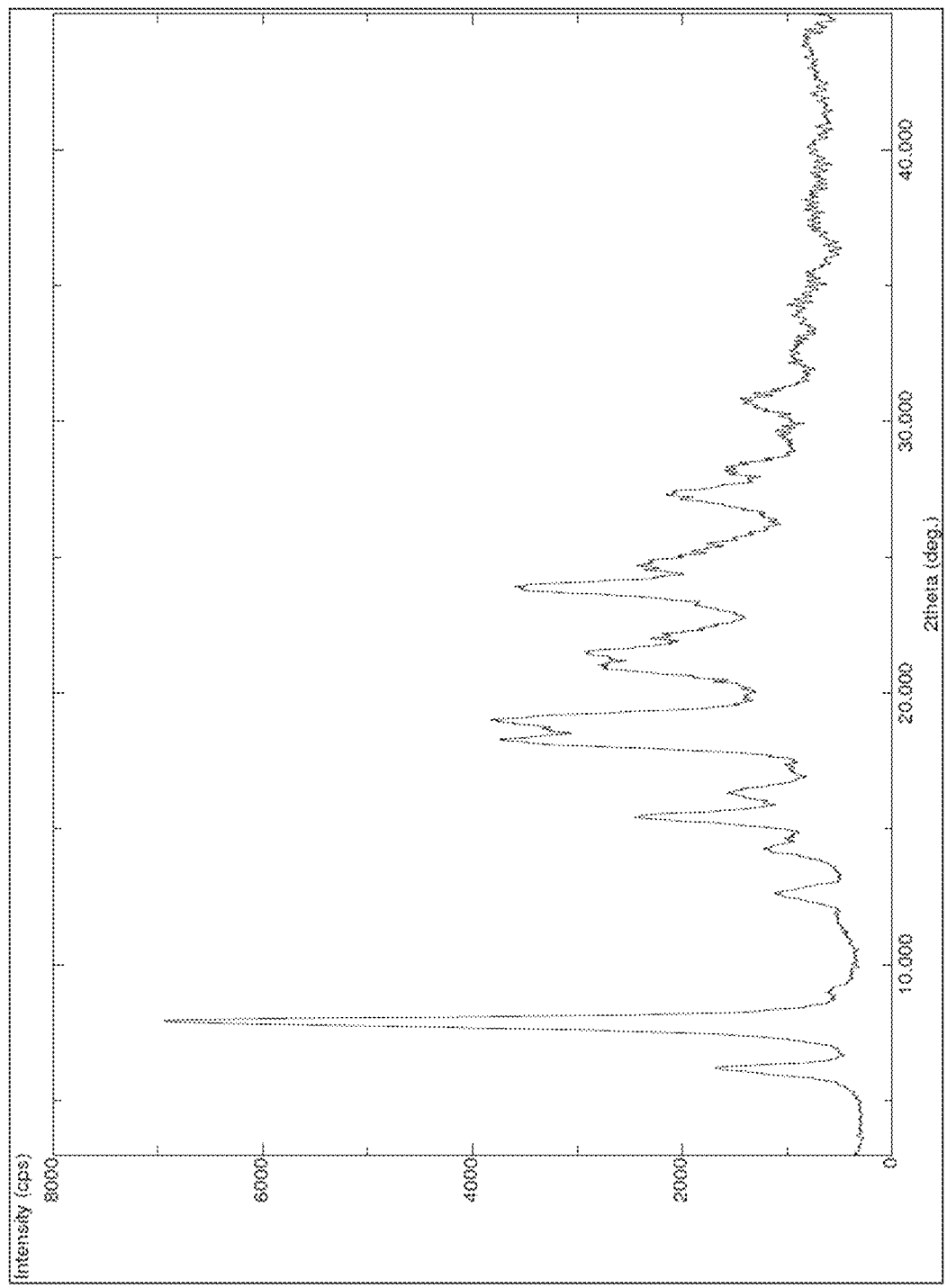
FIG. 23 is the characteristic powder X-ray diffraction (XRD) pattern of crystalline dolutegravir sodium obtained as per example-11.

In another embodiment, the present invention provides a process for preparation of crystalline dolutegravir sodium characterized by a powder X-Ray diffraction pattern having one or more peaks at about 6.2, 7.94, 12.66, 14.18, 15.46, 16.42, 18.26, 19.02, 20.92, 21.52, 22.18, 23.92, 24.68, 27.4, 28.28 and 30.68±0.2° 2θ or characterized by a powder X-Ray diffraction (PXRD) pattern substantially in accordance with FIG. 23, which comprise of de-solvating dolutegravir sodium isobutanol solvate (Form-L11, characterized by a powder X-Ray diffraction pattern having one or more peaks at about 6.08, 6.92, 11.20, 12.48, 14.00, 16.04, 18.24, 19.08, 20.20, 20.90, 22.12, 22.70, 22.96, 23.54, 24.08, 25.84, 26.92, 29.84 and 31.68±0.2° 2θ) by heating at a suitable temperature of about 110° C. to about 135° C., preferably at about 120° C. to about 125° C. for a sufficient period of time, preferably for 4 hrs to 12 hrs under vacuum.

In another embodiment, the present invention provides novel solvates of dolutegravir and their polymorphic forms.

In another embodiment, the present invention provides morpholine solvate of dolutegravir.

In another embodiment, the present invention provides morpholine solvate of dolutegravir in crystalline form.

In another embodiment, the present invention provides crystalline Form-1 of dolutegravir morpholine solvate.

Figure 13:
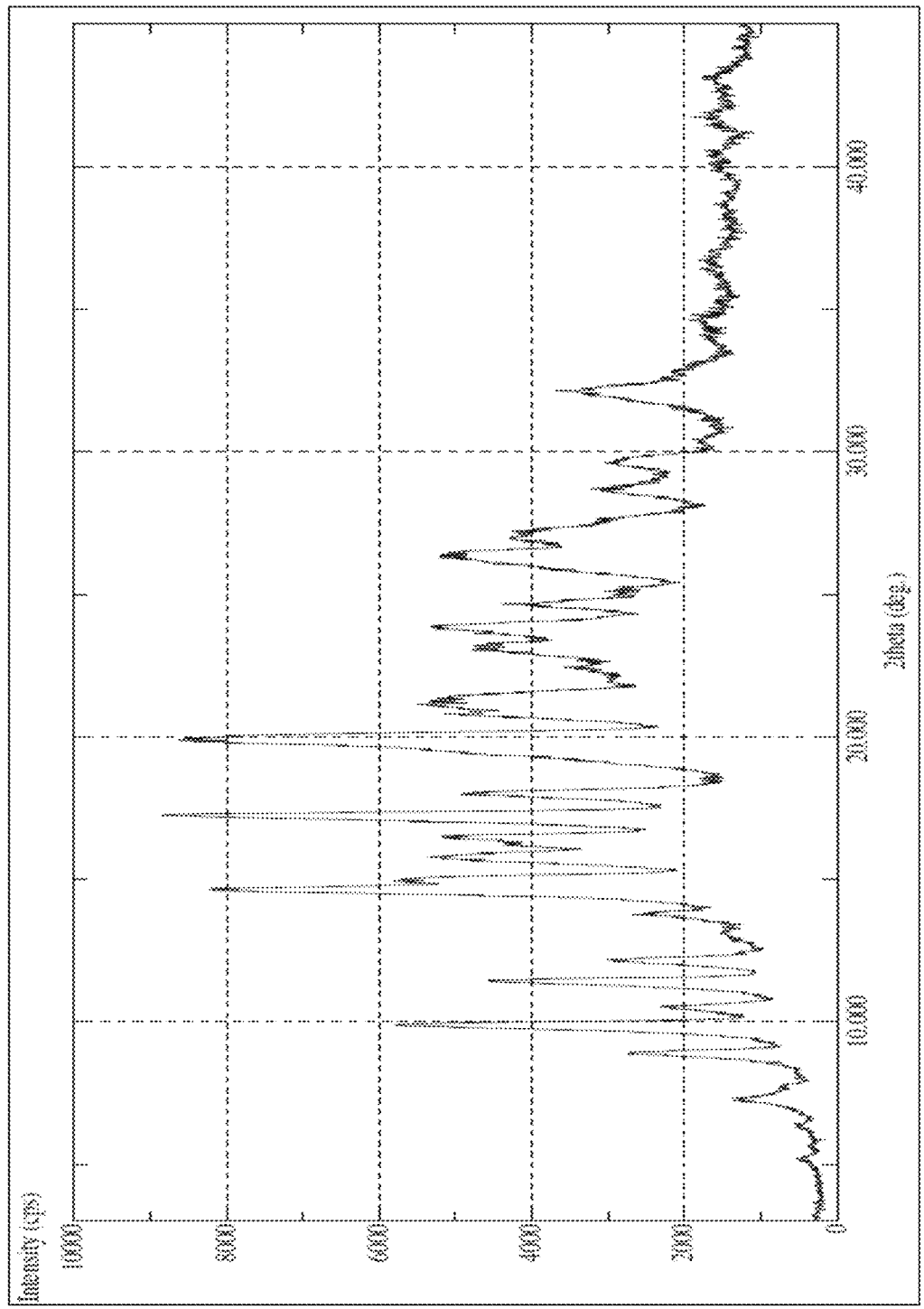
FIG. 13 is the characteristic powder X-ray diffraction (XRD) pattern of crystalline Form-I of dolutegravir morpholine solvate.

In another embodiment, the present invention provides crystalline Form-I of dolutegravir morpholine solvate, characterized by a powder X-Ray diffraction (PXRD) pattern substantially in accordance with FIG. 13.

In another embodiment, the present invention provides crystalline Form-I of dolutegravir morpholine solvate, characterized by a powder X-Ray diffraction pattern having one or more peaks at about 6.30, 7.28, 8.86, 9.90, 10.52, 11.44, 12.14, 13.76, 14.62, 15.04, 15.76, 16.50, 17.24, 18.00, 19.88, 20.76, 21.08, 22.48, 23.24, 23.84, 24.62, 25.04, 26.46, 26.94, 28.60, 29.58 and 32.14±0.2° 2θ.

Figure 14:
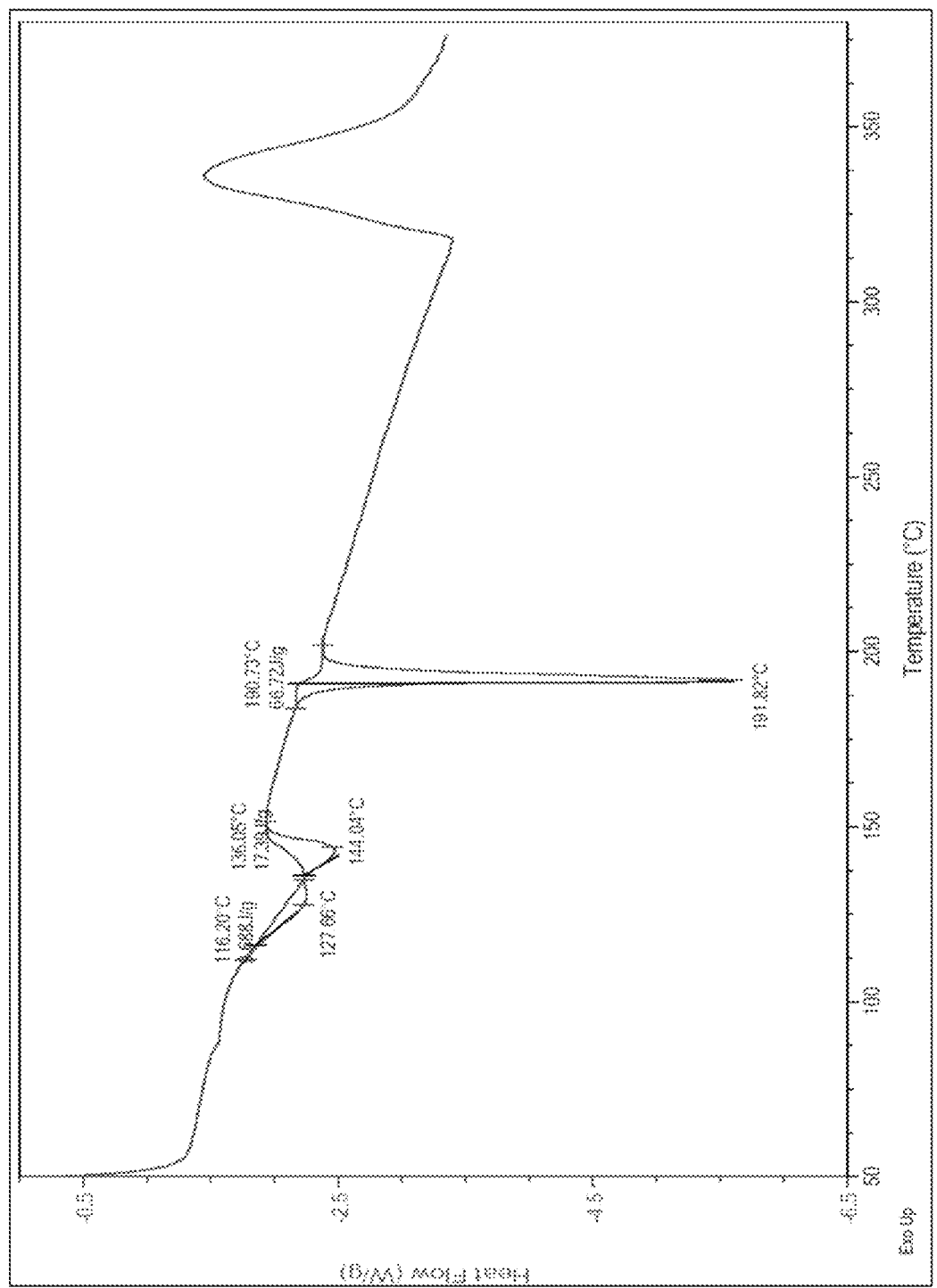
FIG. 14 is the characteristic differential scanning calorimetric (DSC) thermogram of crystalline Form-I of dolutegravir morpholine solvate.

In another embodiment, the present invention provides crystalline Form-I of dolutegravir morpholine solvate, characterized by a differential scanning calorimetry (DSC) substantially in accordance with FIG. 14.

Figure 15:
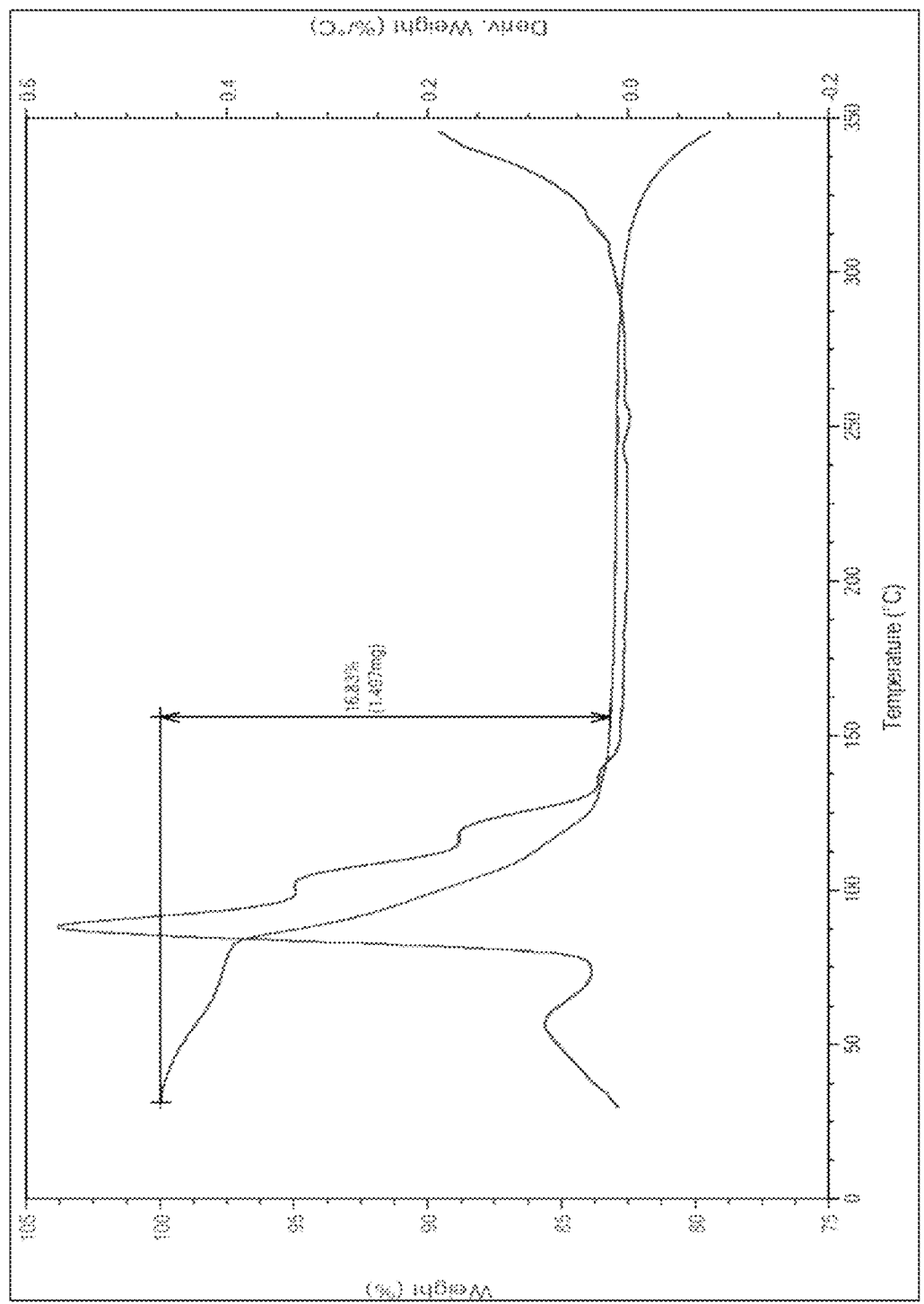
FIG. 15 is the characteristic thermo gravimetric analysis (TGA) of crystalline Form-I of dolutegravir morpholine solvate.

In another embodiment, the present invention provides crystalline Form-I of dolutegravir morpholine solvate, characterized by a thermo gravimetric analysis (TGA) substantially in accordance with FIG. 15.

In another embodiment, the present invention provides crystalline Form-I of dolutegravir morpholine solvate, characterized by a powder X-Ray diffraction (PXRD) pattern substantially in accordance with FIG. 13, a differential scanning calorimetry (DSC) substantially in accordance with FIG. 14 and/or a thermo gravimetric analysis (TGA) substantially in accordance with FIG. 15.

In another embodiment, the present invention provides a process for preparation of crystalline Form-I of dolutegravir morpholine solvate, which comprise of
a) dissolving dolutegravir in a suitable chloro solvent,
b) adding morpholine to step a) solution,
c) adding a suitable anti-solvent to step b) solution, and
d) isolating the dolutegravir crystalline Form-I.

In the aforementioned process of crystalline Form-I of dolutegravir morpholine solvate, dissolution of dolutegravir in a suitable chloro solvents such as methylene chloride, chloroform and the like; preferably methylene chloride, can be carried out at a suitable temperature of about 25° C. to about 45° C., preferably at about 25° C. to about 35° C. In step b) morpholine was added to step a) solution at about 25° C. to about 35° C. The suitable anti-solvents selected from ether solvents such as diethylether, diisopropylether, methyl tertiary butyl ether, ethyl tertiary butyl ether, and the like; preferably methyl tertiary butyl ether, was added to step b) solution at about 25° C. to about 35° C. and the obtained suspension was stirred for 1 hrs to 2 hrs. Then the isolation of crystalline Form I from the reaction mass can be carried out by any conventional techniques known in the art, for example filtration and followed by drying.

In another embodiment, the present invention provides crystalline Form-II of dolutegravir morpholine solvate.

Figure 16:
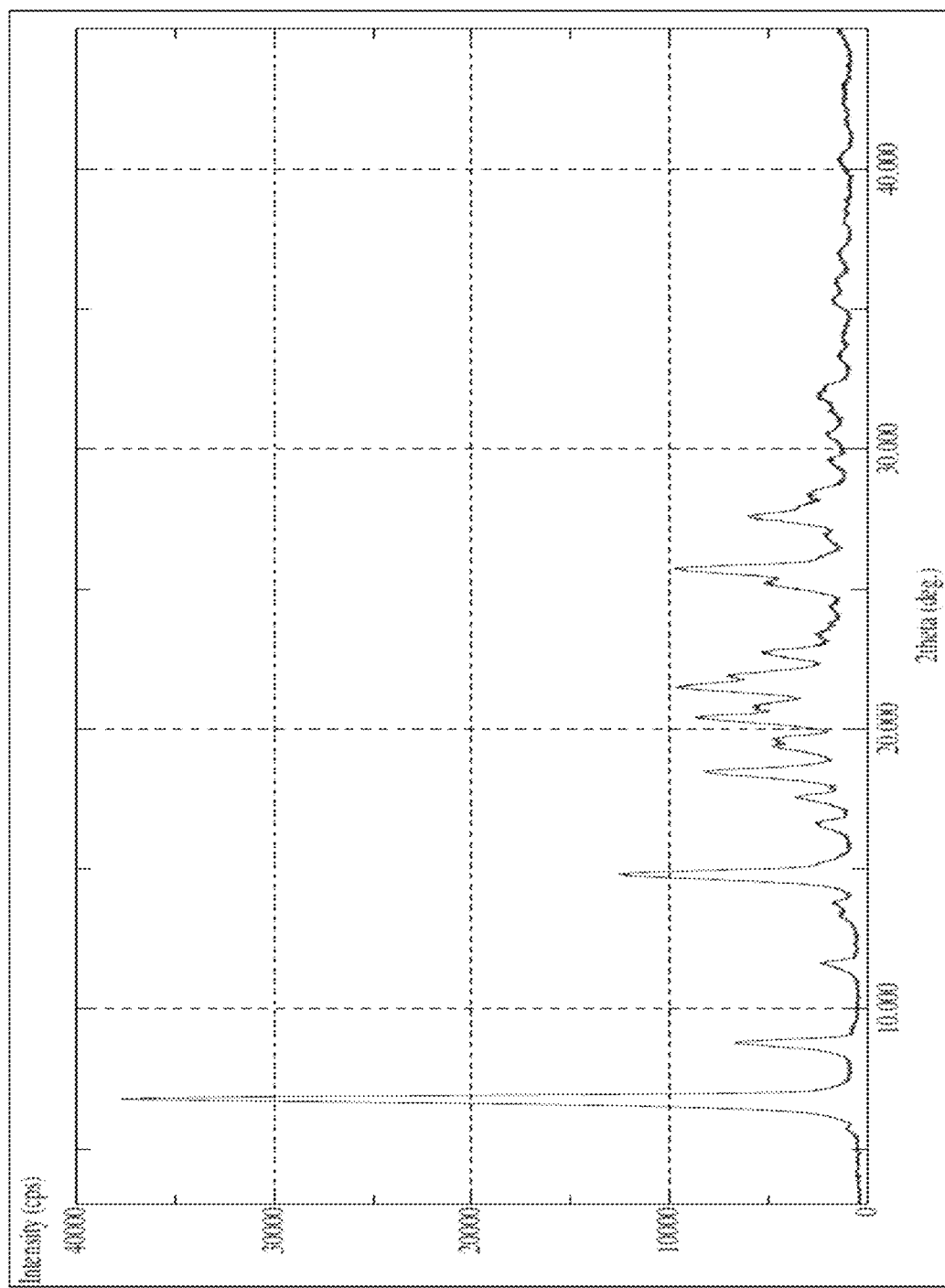
FIG. 16 is the characteristic powder X-ray diffraction (XRD) pattern of crystalline Form-II of dolutegravir morpholine solvate.

In another embodiment, the present invention provides crystalline Form-II of dolutegravir morpholine solvate, characterized by a powder X-Ray diffraction (PXRD) pattern substantially in accordance with FIG. 16.

In another embodiment, the present invention provides crystalline Form-II of dolutegravir morpholine solvate, characterized by a powder X-Ray diffraction pattern having one or more peaks at about 6.78, 8.80, 11.56, 13.76, 14.80, 16.64, 17.56, 18.48, 19.34, 19.66, 20.40, 20.80, 21.48, 21.90, 22.74, 23.38, 25.24, 25.72, 27.56, 28.44, 29.54, 30.48 and 31.88±0.2° 2θ.

Figure 17:
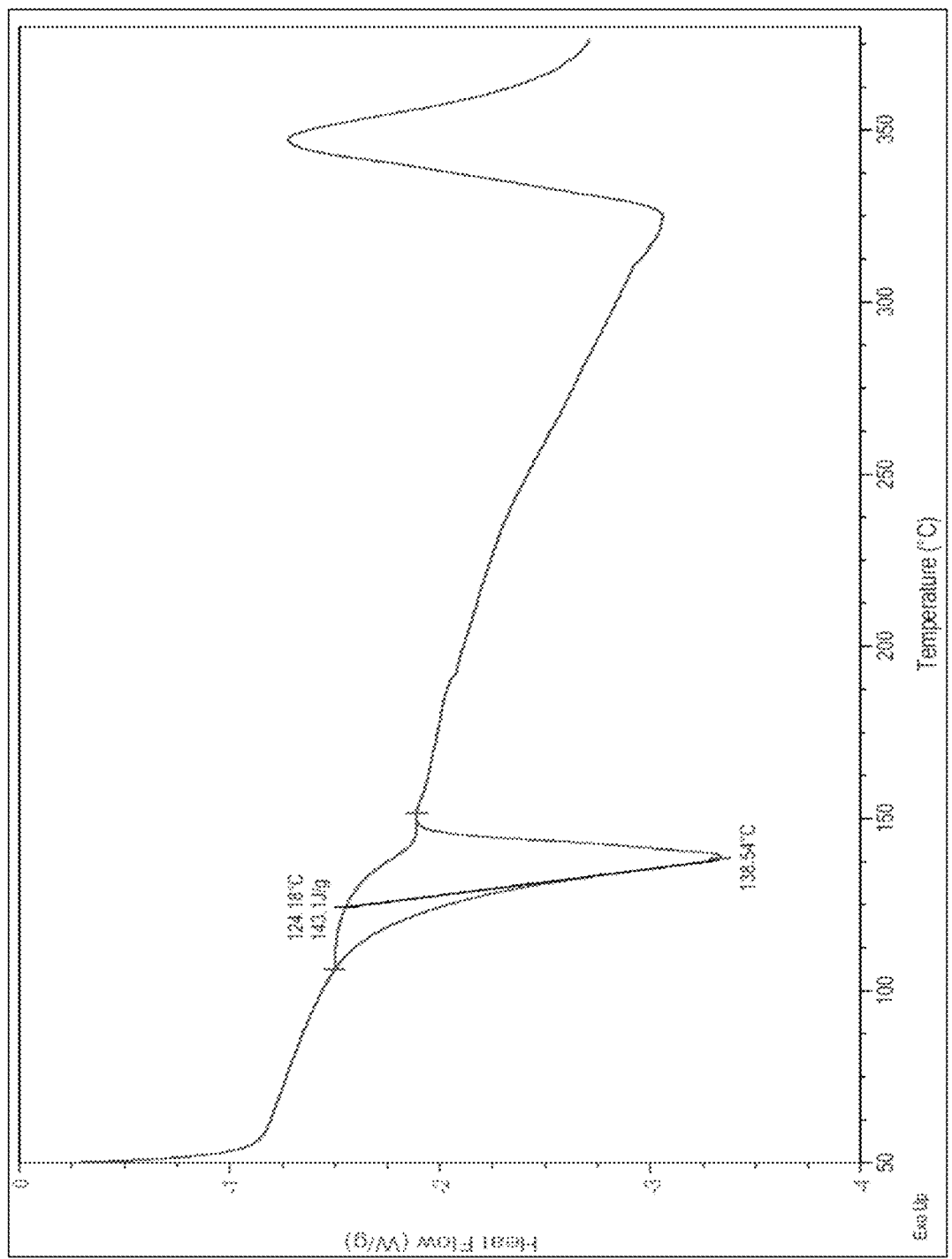
FIG. 17 is the characteristic differential scanning calorimetric (DSC) thermogram of crystalline Form-II of dolutegravir morpholine solvate.

In another embodiment, the present invention provides crystalline Form-II of dolutegravir morpholine solvate, characterized by a differential scanning calorimetry (DSC) substantially in accordance with FIG. 17.

Figure 18:
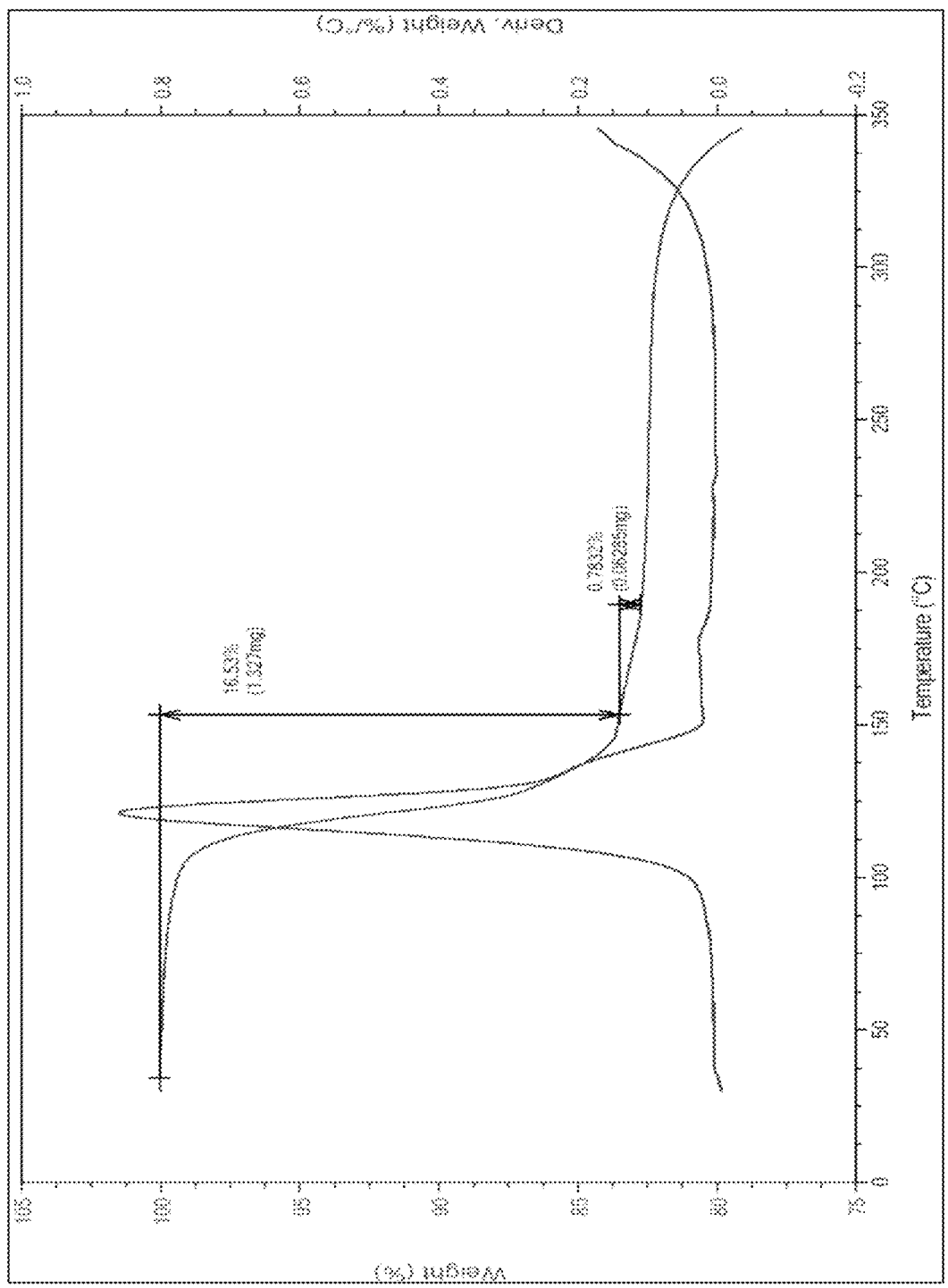
FIG. 18 is the characteristic thermo gravimetric analysis (TGA) of crystalline Form-II of dolutegravir morpholine solvate.

In another embodiment, the present invention provides crystalline Form-II of dolutegravir morpholine solvate, characterized by a thermo gravimetric analysis (TGA) substantially in accordance with FIG. 18.

In another embodiment, the present invention provides crystalline Form-II of dolutegravir morpholine solvate, characterized by a powder X-Ray diffraction (PXRD) pattern substantially in accordance with FIG. 16, a differential scanning calorimetry (DSC) substantially in accordance with FIG. 17 and/or a thermo gravimetric analysis (TGA) substantially in accordance with FIG. 18.

In another embodiment, the present invention provides a process for the preparation of crystalline Form-II of dolutegravir morpholine solvate, which comprise of
a) dissolving dolutegravir in morpholine, and
b) isolating the dolutegravir crystalline Form-II.

In the aforementioned process of crystalline Form-II of dolutegravir morpholine solvate, dissolution of dolutegravir in morpholine can be carried out at a suitable temperature of about 25° C. to about 45° C., preferably at about 25° C. to about 35° C. and the reaction mass is stirred for 15 to 30 mins at about 25° C. to about 35° C. Then the isolation of crystalline Form II from the reaction mass can be carried out by any conventional techniques known in the art, for example filtration and followed by drying. Advantageously before the isolation step b), suitable ether solvents such as diethylether, diisopropylether, methyl tertiary butyl ether, ethyl tertiary butyl ether, and the like; was added to the reaction mass at about 25° C. to about 35° C., stirred for an hour and then filtered.

In another embodiment, the present invention provides 1-amino-2-propanol solvate of dolutegravir.

In another embodiment, the present invention provides 1-amino-2-propanol solvate of dolutegravir in crystalline form.

Figure 19:
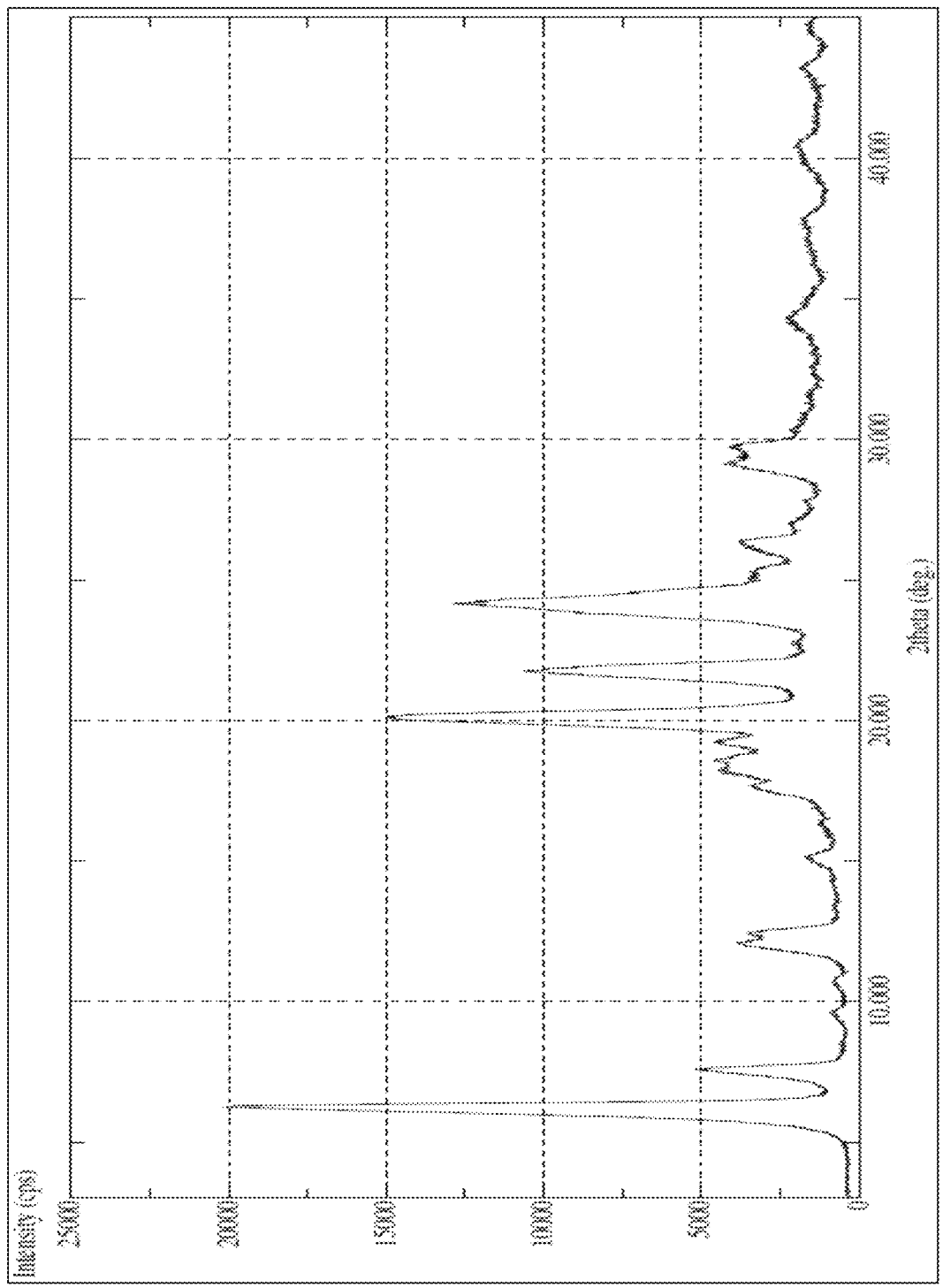
FIG. 19 is the characteristic powder X-ray diffraction (XRD) pattern of crystalline form of dolutegravir 1-amino-2-propanol solvate.

In another embodiment, the present invention provides crystalline form of dolutegravir 1-amino-2-propanol solvate, characterized by a powder X-Ray diffraction (PXRD) pattern substantially in accordance with FIG. 19.

In another embodiment, the present invention provides crystalline form of dolutegravir 1-amino-2-propanol solvate, characterized by a powder X-Ray diffraction pattern 35 having one or more peaks at about 6.26, 7.58, 9.64, 12.04, 12.44, 15.18, 17.62, 18.20, 18.58, 19.22, 20.10, 21.76, 24.16, 25.34, 26.08, 26.34, 26.96, 29.10, 29.74 and 34.30±0.2° 2θ.

Figure 20:
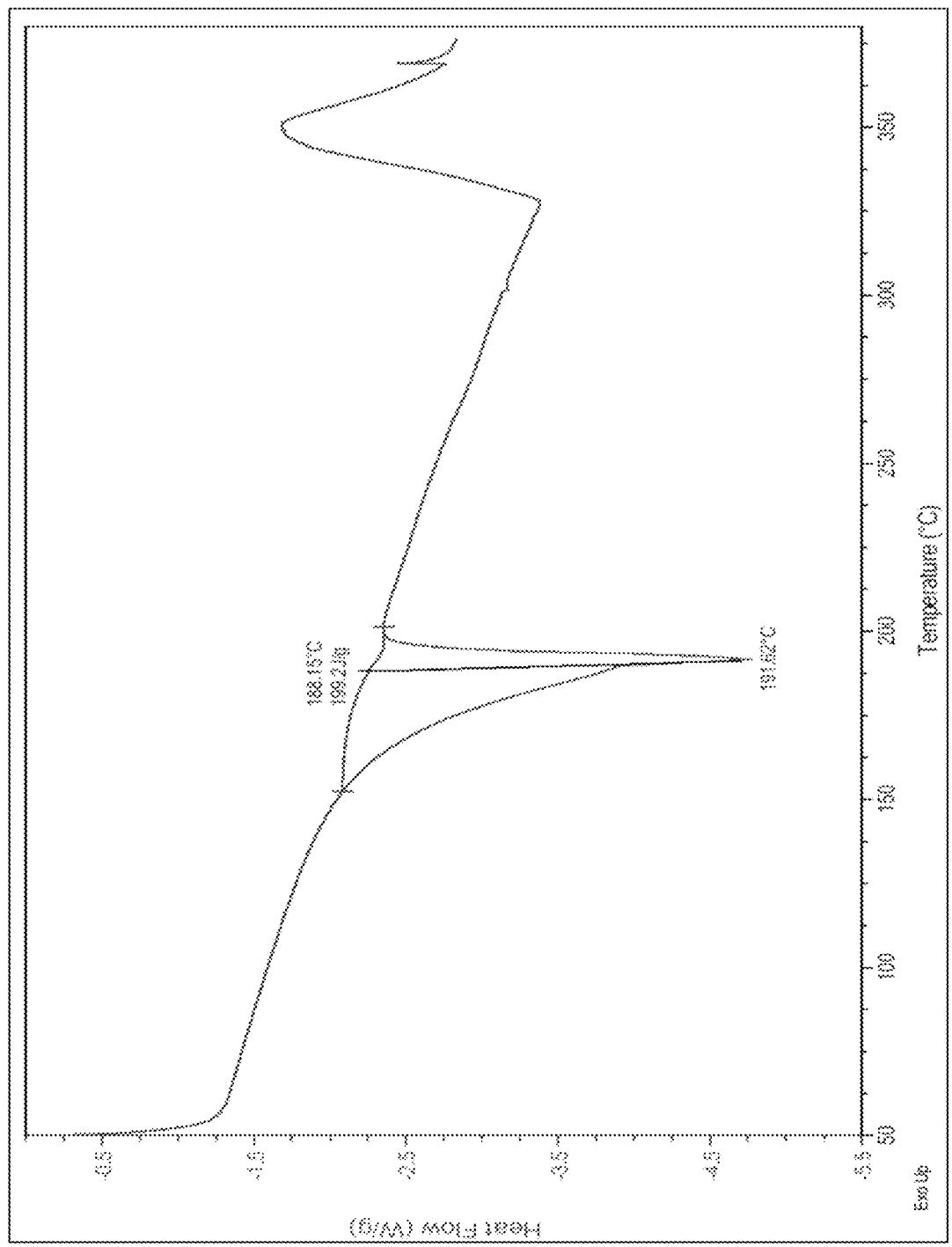
FIG. 20 is the characteristic differential scanning calorimetric (DSC) thermogram of crystalline form of dolutegravir 1-amino-2-propanol solvate.

In another embodiment, the present invention provides crystalline form of dolutegravir 1-amino-2-propanol solvate, characterized by a differential scanning calorimetry (DSC) substantially in accordance with FIG. 20.

Figure 21:
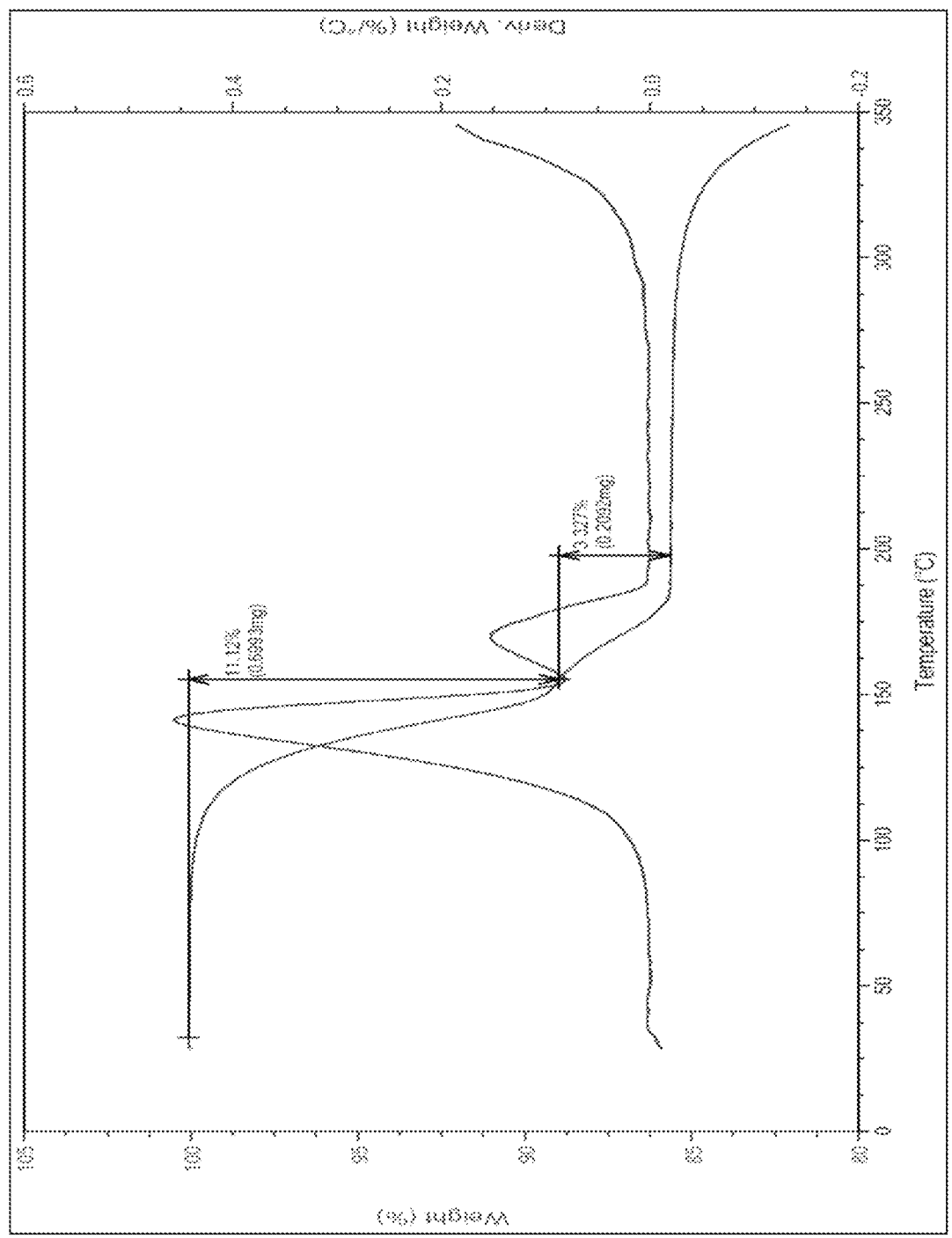
FIG. 21 is the characteristic thermo gravimetric analysis (TGA) of crystalline form of dolutegravir 1-amino-2-propanol solvate.

In another embodiment, the present invention provides crystalline form of dolutegravir 1-amino-2-propanol solvate, characterized by a thermo gravimetric analysis (TGA) substantially in accordance with FIG. 21.

In another embodiment, the present invention provides crystalline form of dolutegravir 1-amino-2-propanol solvate, characterized by a powder X-Ray diffraction (PXRD) pattern substantially in accordance with FIG. 19, a differential scanning calorimetry (DSC) substantially in accordance with FIG. 20 and/or a thermo gravimetric analysis (TGA) substantially in accordance with FIG. 21.

In another embodiment, the present invention provides a process for the preparation of crystalline form of dolutegravir 1-amino-2-propanol solvate, which comprise of
a) dissolving dolutegravir in a suitable solvent,
b) adding 1-amino-2-propanol to step a) solution; and
c) isolating the crystalline form of dolutegravir 1-amino-2-propanol solvate.

In the aforementioned process of crystalline form of dolutegravir 1-amino-2-propanol solvate, dissolution of dolutegravir in a suitable solvent such as N-methyl-2-pyrrolidone or methylene chloride, can be carried out at a suitable temperature of about 25° C. to about 45° C., preferably at about 25° C. to about 35° C. In step b) 1-amino-2-propanol was added to step a) solution at about 25° C. to about 35° C. and the obtained suspension stirred for a sufficient period of time, preferably for 30 mins to 2 hrs. Then the isolation of crystalline dolutegravir 1-amino-2-propanol solvate from the reaction mass can be carried out by any conventional techniques known in the art, for example filtration and followed by drying. Advantageously water was added to the reaction mass at about 25° C. to about 35° C. before the isolation step and stirred for an hour then filtered.

As used herein above, the dolutegravir which is used as a starting material is known in the art and can be prepared by any known method. The starting dolutegravir may be in any form such as crude obtained directly from the reaction mass, crystalline, amorphous or other forms of dolutegravir, including various solvates and hydrates known in the art.

The novel polymorphs of dolutegravir sodium and solvates of dolutegravir of the present invention are stable even at accelerated conditions and having higher dissolution rate when compared to known solid forms of dolutegravir sodium.

In another embodiment, the present invention provides a pharmaceutical composition comprising novel polymorphic forms of dolutegravir sodium and solvates of dolutegravir of the present invention and at least one pharmaceutically acceptable excipient.

In a preferred embodiment, the present invention provides a pharmaceutical composition comprising crystalline dolutegravir sodium Form-L9 and at least one pharmaceutically acceptable excipient.

The X-Ray powder diffraction of novel polymorphs of the present invention can be measured by an X-ray powder Diffractometer equipped with a Cu-anode ([λ]=1.54 Å), X-ray source operated at 30 kV, 15 mA and a Ni filter is used to strip K-beta radiation. The sample was analyzed using the following instrument parameters: measuring range=3-45° 2θ; step width=0.020°; and scan speed=5°/minute.

All DSC data reported herein were analyzed in hermitically sealed aluminium pan with pin hole, with a blank hermitically sealed aluminium pan with pin hole as the reference and were obtained using DSC (DSC Q200, TA instrumentation, Waters) at a scan rate of 10° C. per minute with an Indium standard.

All TGA data reported herein were analyzed using TGA Q500 V 20.2 build 27 in platinum pan with a temperature rise of about 10° C./min in the range of about 30° C. to about 250° C.

Other embodiments of the invention include composition containing one or more polymorphic forms of dolutegravir or salts thereof as described above. The pharmaceutical composition includes, but is not limited to tablets, capsules, solutions, suspensions and injections. Such pharmaceutical compositions contains one or more excipients, including, without limitation, binders such as binders such as acacia, guar gum, tragacanth, gelatin, polyvinylpyrrolidone, hydroxypropyl celluloses, hydroxypropyl starch, hydroxypropylmethyl celluloses, pregelatinized starch and the like; diluents/fillers such as starch, pregelatinized starch, lactose, powdered cellulose, microcrystalline cellulose, silicified microcrystalline cellulose, dicalcium phosphate, tricalcium phosphate, magnesium oxide, magnesium carbonate, calcium carbonate, mannitol, sorbitol, xylitol, sugar, and the like; lubricants such as stearic acid, talc, magnesium stearate, calcium stearate, zinc stearate, sodium stearyl fumarate and the like; disintegrants such as starch, sodium starch glycolate, pregelatinized starch, crospovidone, polacrilin potassium, croscarmellose sodium, colloidal silicon dioxide and the like; glidants such as colloidal silicon dioxide, talc and the like; wetting agents such as sodium lauryl sulfate, sodium dodecyl sulfate, tween and the like; emulsifiers, suspending agents, sweeteners, flavorings, preservatives, buffers, effervescent agents, and other conventional excipients and additives.

The following examples are provided by way of illustration only, and are not intended to be limiting of the present invention. Further, the present invention covers all the possible combinations of particular and preferred embodiments indicated herein.

EXAMPLES

Example-1: Preparation of Dolutegravir Sodium Form-L9

Dolutegravir sodium Form-L12 (1 g) was dried at 120-125° C. for 8 hrs under vacuum yielded dolutegravir sodium Form-L9. Yield: 880 mg The XRPD is set forth in FIG. 1; The DSC is set forth in FIG. 2; The TGA is set forth in FIG. 3.

Example-2: Preparation of Dolutegravir Sodium Form-L9

Dolutegravir (100 g) was added to 1-pentanol (1500 ml) at 25-35° C. To this mixture, 6.6N sodium hydroxide solution (39.73 ml) was slowly added at 22-28° C., then the reaction mass was stirred for about 40 hrs at 22-28° C. The solid obtained was filtered, washed with 1-pentanol and suck dried. The suck dried material was initially dried at 25-35° C. for 2 hrs under vacuum, further at 50-55° C. for 10 hrs under vacuum and finally dried at 100-110° C. for 16 hrs under vacuum. The dried compound was kept in a air tray drier at 25-35° C. for about 6 hrs yielded dolutegravir sodium Form-L9. Yield: 90 grams Example-3: Preparation of Dolutegravir Sodium Form-L10

Dolutegravir (1 g) was added to 10% aqueous isopentanol (10 ml) at 25-35° C. To this suspension, aqueous sodium hydroxide (6.75N, 0.1 ml) was added at 25-35° C. and stirred for 8 hrs. The solid obtained was filtered, washed with isopentanol, suck dried and finally dried at 50-55° C. for 4 hrs under vacuum to get the title compound. Yield: 1.1 g The XRPD is set forth in FIG. 4; The DSC is set forth in FIG. 5; The TGA is set forth in FIG. 6.

Example-4: Preparation of Dolutegravir Sodium Form-L11

Dolutegravir (2 g) was added to isobutanol (30 ml) at 25-35° C. To this suspension, aqueous sodium hydroxide (6.75N, 0.8 ml) was added and heated to 60-65° C. The reaction mass was stirred for 3 hrs at 60-65° C. and then cooled to 25-35° C. The solid obtained was filtered, washed with isobutanol and dried at 50-55° C. for 2 hrs under vacuum to get the title compound. Yield: 2.2 g The XRPD is set forth in FIG. 7; The DSC is set forth in FIG. 8; The TGA is set forth in FIG. 9.

Example-5: Preparation of Dolutegravir Sodium Form-L11

Dolutegravir (2 g) was added to isobutanol (30 ml) at 25-35° C. To this suspension, aqueous sodium hydroxide (6.75N, 0.8 ml) was added at 25-35° C. and stirred for 15 hrs. The solid obtained was filtered, washed with isobutanol, suck dried and finally dried at 50-55° C. for 2 hrs under vacuum to get the title compound. Yield: 2.4 g

Example-6: Preparation of Dolutegravir Sodium Form-L12

Dolutegravir (1 g) was added to 1-pentanol (10 ml) at 25-35° C. To this suspension, aqueous sodium hydroxide (6.75N, 0.4 ml) was added at 25-35° C. and stirred for 8 hrs. The solid obtained was filtered, washed with 1-pentanol and dried at 50-55° C. for 4 hrs under vacuum to get the title compound. Yield: 1.2 g The XRPD is set forth in FIG. 10; The DSC is set forth in FIG. 11; The TGA is set forth in FIG. 12.

Example-7: Preparation of Crystalline Form-I of Dolutegravir Morpholine Solvate Dolutegravir (1 g) was dissolved in methylene chloride (10 ml) at 25-35° C. To this solution, morpholine (0.4 ml) was added and stirred for 10 mins. Methyl tertiary butyl ether (30 ml) was added to the reaction mass at 25-35° C. and stirred for 75 mins. The solid obtained was filtered, washed with methyl tertiary butyl ether and dried at 50-55° C. for 3 hrs to get the title compound. Yield: 1.2 g The XRPD is set forth in FIG. 13; The DSC is set forth in FIG. 14; The TGA is set forth in FIG. 15.

Example-8: Preparation of Crystalline Form-II of Dolutegravir Morpholine Solvate Dolutegravir (10 g) was dissolved in morpholine (100 ml) at 25-35° C. and stirred for 15 mins. Methyl tertiary butyl ether (500 ml) was added to the reaction mass at 25-35° C. and stirred for an hour. The solid obtained was filtered, washed with methyl tertiary butyl ether and suck dried to get the title compound. Yield: 12.9 g The XRPD is set forth in FIG. 16; The DSC is set forth in FIG. 17; The TGA is set forth in FIG. 18.

Example-9: Preparation of Crystalline Form of Dolutegravir 1-Amino-2-Propanol Solvate Dolutegravir (3 g) was dissolved in N-methyl-2-pyrrolidone (15 ml) at 25-35° C. To this solution, 1-amino-2-propanol (1.1 ml) was added and the obtained suspension was stirred for 10 mins at 25-35° C. DM water (30 ml) was added to the reaction mass at 25-35° C. and stirred for 1.5 hr. The solid obtained was filtered, washed with water and dried at 50-55° C. under vacuum for 4 hrs to get the title compound. Yield: 2.4 g The XRPD is set forth in FIG. 19; The DSC is set forth in FIG. 20, The TGA is set forth in FIG. 21.

Example-10: Preparation of Crystalline Dolutegravir Sodium

Dolutegravir sodium Form-L10 (1 g) was dried at 120-125° C. for 8 hrs under vacuum yielded crystalline dolutegravir sodium. Yield: 894 mg The XRPD is set forth in FIG. 22.

Example-11: Preparation of Crystalline Dolutegravir Sodium

Dolutegravir sodium Form-L11 (2 g) was dried at 120-125° C. for 10 hrs under vacuum yielded crystalline dolutegravir sodium. Yield: 1.8 g The XRPD is set forth in FIG. 23.

Example-12: Stability Data for Dolutegravir Sodium Form-L9

Dolutegravir sodium Form-L9 was packed in a Low density polyethylene (LDPE) bag with a strip seal, which is again kept in a second low density polyethylene bag with strip seal. The LDPE bag is kept in a high density polyethylene (HDPE) container and well closed and loaded for stability chamber.

The stability data performed at 40-2° C./75±5% RH ensures that the dolutegravir sodium Form-L9 of the present invention retained the same polymorphic and chemical identity at least up to three months. This indicates that dolutegravir sodium Form-L9 is physically and chemically stable.

Table-1 shows chemical and polymorphic stability data of dolutegravir sodium Form-L9 when stored at 40±2° C./75±5% RH:

TABLE 1

| Parameters | Initial | 1 month | 2 month | 3 month |
| --- | --- | --- | --- | --- |
| Water content (% w/w) | 2.2 | 1.9 | 2 | 2.3 |
| Purity by HPLC (% w/w) | 99.8 | 99.9 | 99.9 | 99.8 |
| Des fluoro dolutegravir (% w/w) | 0.09 | 0.08 | 0.09 | 0.10 |
| PXRD | Form-L9 | Form-L9 | Form-L9 | Form-L9 |

The purity of dolutegravir sodium was analysed using high performance liquid chromatography ("HPLC") with the conditions is tabulated below:

| | |
| --- | --- |
| Column | Kinetex Phenyl Hexyl (250 × 4.6) mm, 5.0 μm |
| Column temp | 27° C. |
| Mobile phase | A: Buffer, THF and acetonitrile; B: Methanol, water, THF and acetonitrile. |
| Diluent | Acetonitrile and water |
| Flow rate | 0.8 ml/min |
| Wavelength | 258 nm |
| Injection Volume | 10 μl |

Example-13: Thermal Stability of Dolutegravir Sodium Form-L9

Dolutegravir sodium Form-L9 was kept in an oven at 60° C. and 100° C. for 24 hrs. The samples were analyzed by PXRD and DSC and observed that same polymorphic nature retained after the studies. Table-2 shows polymorphic nature of the dolutegravir sodium Form-L9 at 60° C. and 100° C. for 24 hrs by PXRD and DSC.

TABLE 2

| Initial Form | Temperature | Hours | Form after heating | |
|---|---|---|---|---|
| | | | PXRD | DSC |
| Form-L9 | 60° C. | 24 hrs | Form-L9 | Form-L9 |
| Form-L9 | 100° C. | 24 hrs | Form-L9 | Form-L9 |

Figure 24A:
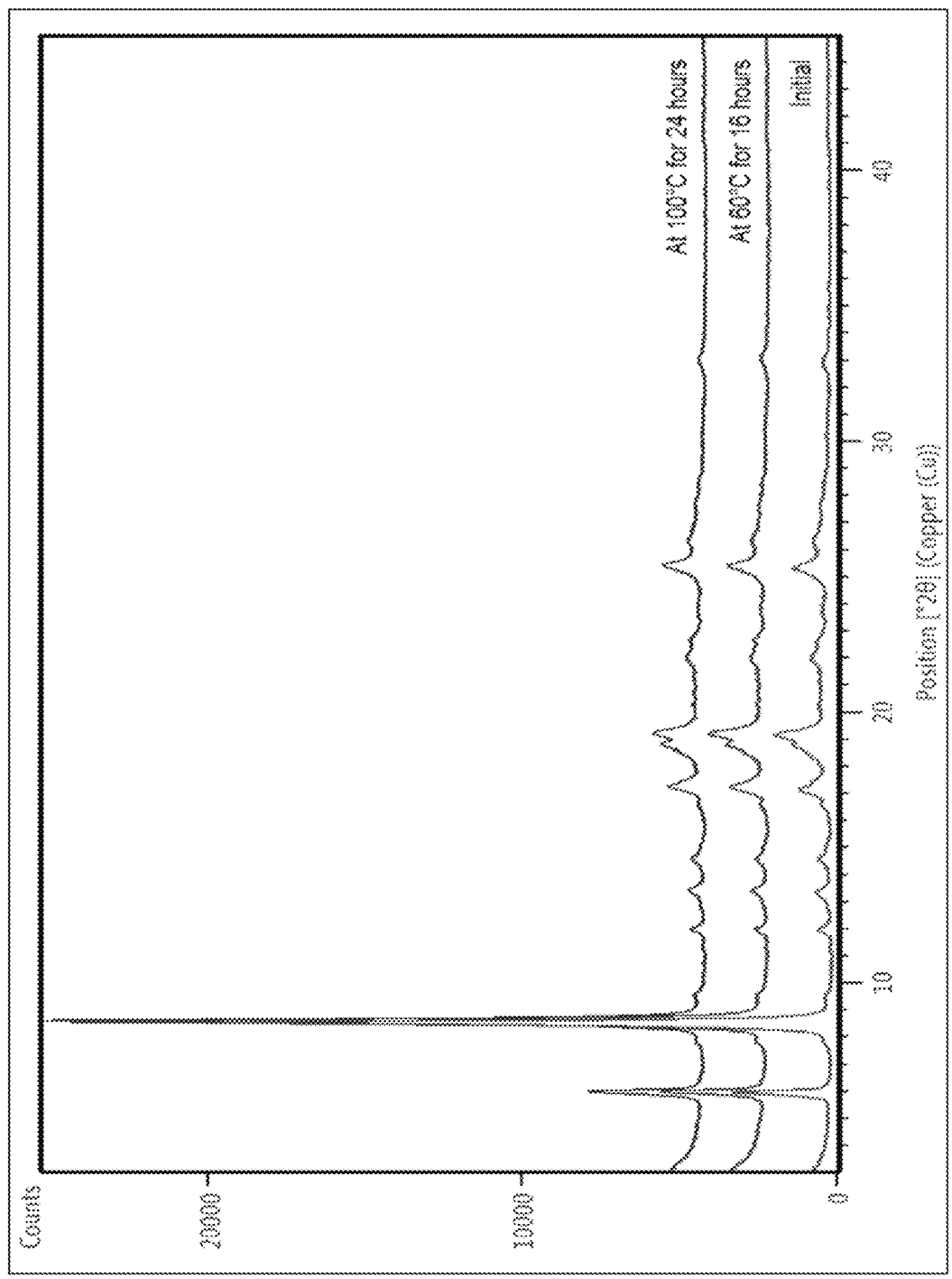
FIG. 24a shows overlaid powder X-ray diffraction (XRD) pattern of dolutegravir sodium Form-L9 under thermal study.
Figure 24B:
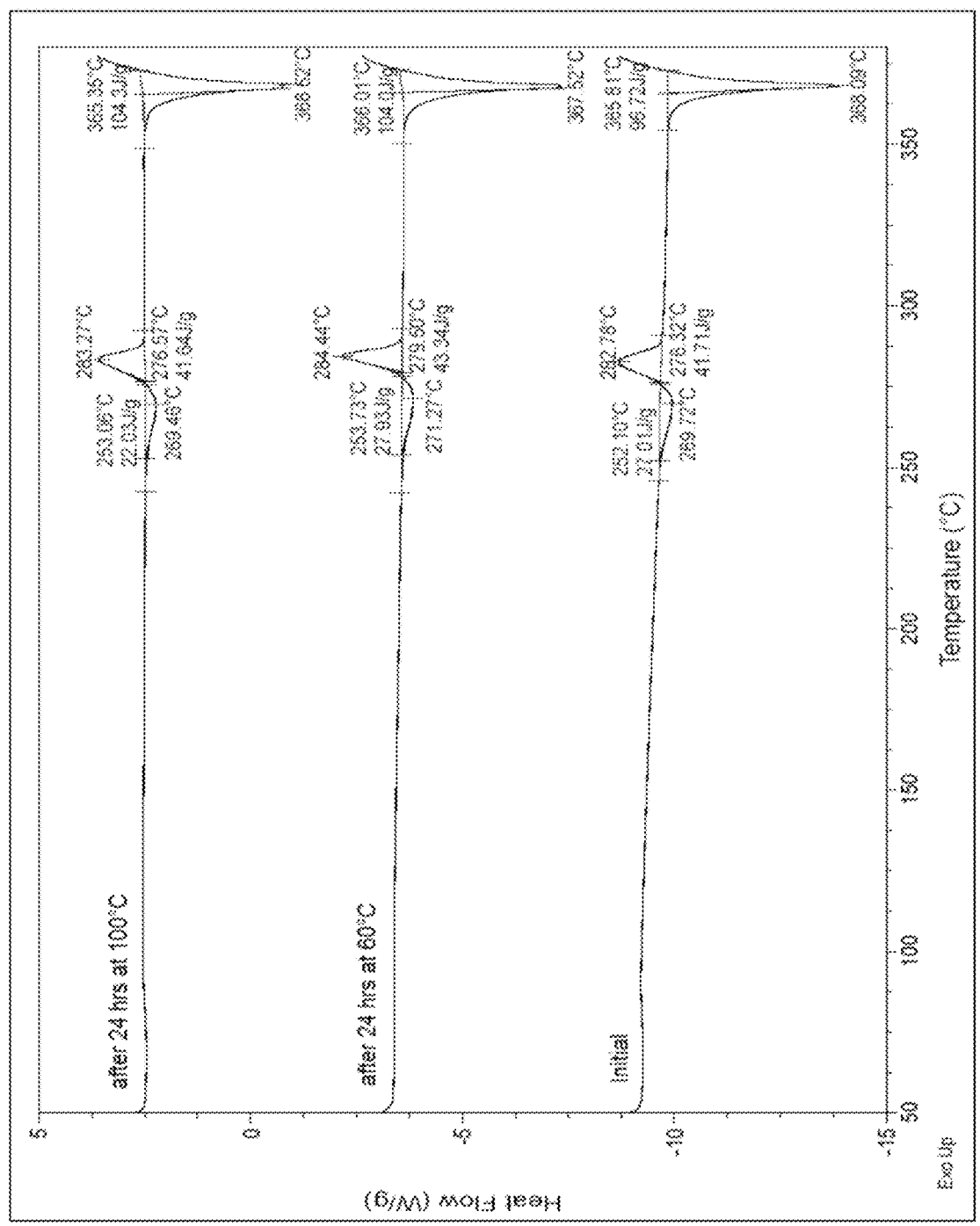
FIG. 24b shows overlaid differential scanning calorimetric (DSC) thermogram of dolutegravir sodium Form-L9 under thermal study.

The analytical data provided in Table-2 suggest that the dolutegravir sodium Form-L9 is stable even at elevated temperatures. Overlaid PXRD pattern and DSC thermogram of dolutegravir sodium Form-L9 subjected to thermal stress study at 60° C. and 100° C. for 24 hours is represented as Figure-24a and Figure-24b respectively.

Example-14: Hygroscopic Study of Dolutegravir Sodium Form-L9

Figure 25:
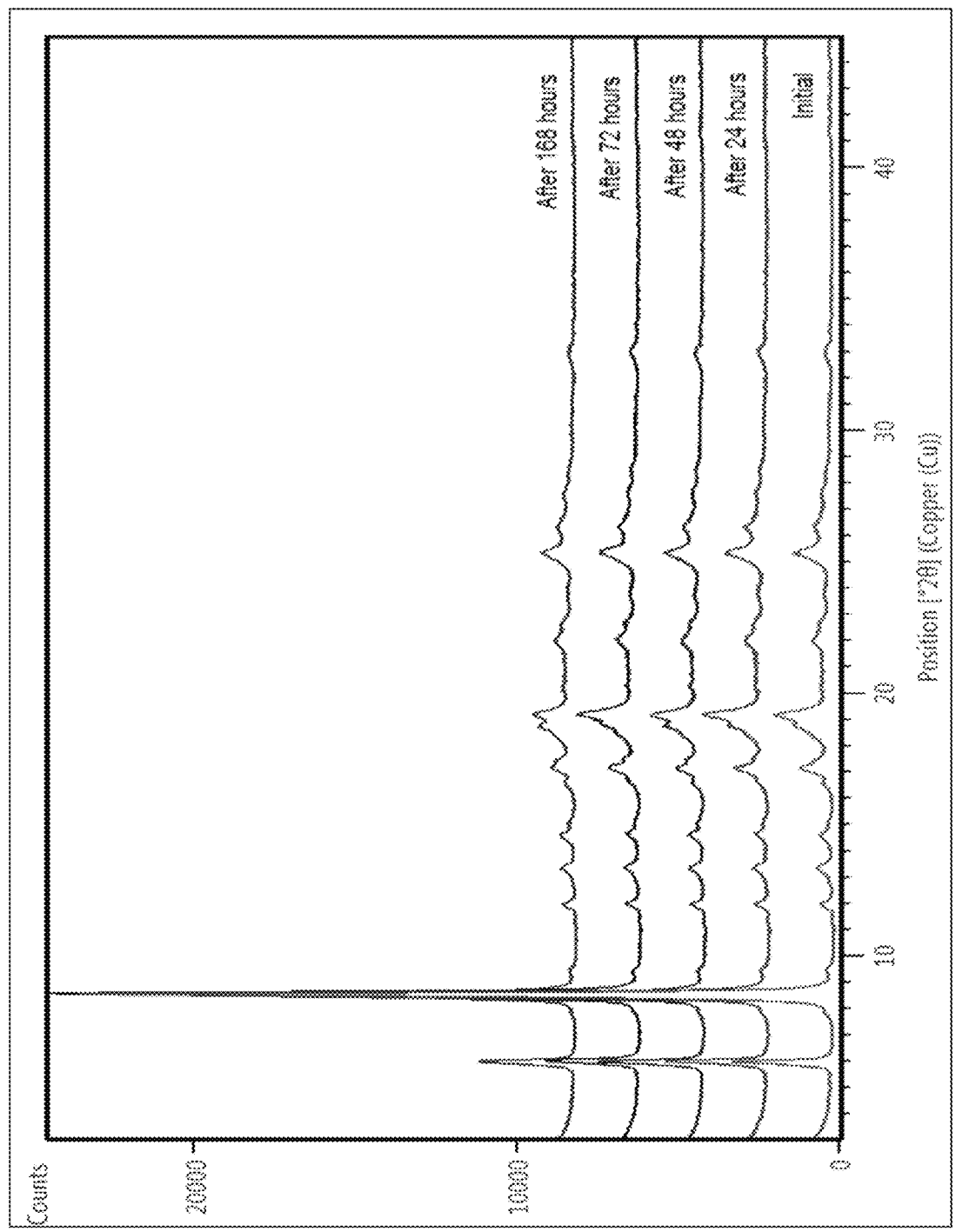
FIG. 25 shows overlaid powder X-ray diffraction (XRD) pattern of dolutegravir sodium Form-L9 subjected to hygroscopic study at 85% RH.

Dolutegravir sodium Form-L9 was exposed to 85% relative humidity at room temperature for one week and was analyzed by PXRD at different time intervals such as 24 hours, 48 hours, 72 hours and 168 hours. The samples were analyzed by PXRD and DSC and observed that same polymorphic nature retained after the studies. The overlaid PXRD pattern of dolutegravir sodium Form-L9 subjected to hygroscopic study at 85% RH is represented as Figure-25.

Example-15: Solubility Studies of Dolutegravir Sodium Form L9

Aqueous solubility was performed for dolutegravir sodium anhydrous form (prepared according to Ex-11 of WO2010/068253) and Form-L9 of the present invention at different pH buffers and solubility profile was found to be comparable. The results of aqueous solubility profile after 24 hours by UV quantification was shown in the following Table-3:

TABLE 3

| S. No | Aqueous buffer solution | Anhydrous Form | Form L9 |
|---|---|---|---|
| 1 | Water | 0.56 | 0.54 |
| 2 | pH buffer 1.2 | 0.53 | 0.54 |
| 3 | pH buffer 4.5 | 0.39 | 0.33 |
| 4 | pH buffer 6.8 | 0.38 | 0.54 |

Example-16

Composition for the preparation of dolutegravir sodium tablets with dolutegravir sodium Form L9.

| S. No | Ingredients | % w/w |
|---|---|---|
| 1 | Dolutegravir Sodium | 15-20 |
| 2 | D-Mannitol | 45-65 |
| 3 | Microcrystalline Cellulose | 15-20 |
| 4 | Sodium Starch Glycolate | 2-8 |
| 5 | Povidone | 2-8 |
| 6 | Sodium Stearyl Fumarate | 0.5-3 |

Tablets are prepared by using direct compression process and the dissolution of dolutegravir sodium tablets are performed in 0.01M pH-6.8 Phosphate buffer+0.25% Sodium lauryl sulfate, 900 mL, Paddle, 50 rpm and the results are as follows:

| Time (Min) | Test (Tablets prepared using Form-L9) | Ref Product (Tivicay) |
|---|---|---|
| 5 | 34 | 30 |
| 10 | 68 | 61 |
| 15 | 88 | 85 |
| 20 | 93 | 92 |
| 30 | 97 | 98 |
| 45 | 99 | 99 |

Example 17: Intrinsic Dissolution Study of Dolutegravir Sodium Form L9

Dissolution experiments were carried out in ELECTRO-LAB-8 dissolution apparatus equipped with an ETC-112 temperature controller. An intrinsic dissolution apparatus (Woods apparatus) was used. Samples were compressed at 2.0 metric tons for 1 min in KBr hydraulic press, giving a sample surface of 0.50 cm$^2$. A dissolution medium consisting of 0.01M pH-6.8 Phosphate buffer+0.25% Sodium lauryl sulfate, 900 mL, Paddle, 50 rpm, was used for each experiment. The results of dissolution studies were shown in Table-4:

TABLE 4

| Time (Min) | Form- L9 | Anhydrous Form |
|---|---|---|
| 15 | 1.17 | 0.18 |
| 30 | 1.56 | 0.24 |
| 45 | 1.64 | 0.26 |
| 60 | 1.77 | 0.23 |
| 120 | 1.98 | 0.43 |
| 480 | 2.23 | 1.72 |
| 1440 | 4.36 | 3.97 |

While the invention has been described with reference to above detailed description and the preferred examples, it is not intended to be limited thereto. Therefore the above description should not be construed as limiting, but merely as exemplifications of preferred embodiments. For example, the functions described above and implemented as the best mode for operating the present invention are for illustration purposes only. Other arrangements and methods may be implemented by those skilled in the art without departing from the scope and spirit of this invention. Moreover, those skilled in the art will envision other modifications within the scope and spirit of the specification appended hereto.

We claim:

1. Dolutegravir 1-amino-2-propanol solvate.

2. Crystalline form of dolutegravir 1-amino-2-propanol solvate, characterized by a powder X-Ray diffraction pattern having one or more peaks at about 6.26, 7.58, 9.64, 12.04, 12.44, 15.18, 17.62, 18.20, 18.58, 19.22, 20.10, 21.76, 24.16, 25.34, 26.08, 26.34, 26.96, 29.10, 29.74 and 34.30±0.2° 2θ.

3. Crystalline form of dolutegravir 1-amino-2-propanol solvate of claim 2, further characterized by one or more of a powder X-Ray diffraction (PXRD) pattern substantially in accordance with FIG. 19, a differential scanning calorimetry (DSC) substantially in accordance with FIG. 20, and a thermo gravimetric analysis (TGA) substantially in accordance with FIG. 21.

4. A process for the preparation of crystalline form of dolutegravir 1-amino-2-propanol solvate, which comprises:
 a) dissolving dolutegravir in a suitable solvent;
 b) adding 1-amino-2-propanol to step a) solution; and
 c) isolating the crystalline form of dolutegravir 1-amino-2-propanol solvate.

5. The process of claim 4, wherein the suitable solvent is selected from N-methyl-2-pyrrolidone or methylene chloride.

6. A pharmaceutical composition comprising:
 dolutegravir 1-amino-2-propanol solvate; and
 at least one pharmaceutically acceptable excipient,
 wherein the dolutegravir 1-amino-2-propanol solvate is characterized by a powder X-Ray diffraction pattern having one or more peaks at about 6.26, 7.58, 9.64, 12.04, 12.44, 15.18, 17.62, 18.20, 18.58, 19.22, 20.10, 21.76, 24.16, 25.34, 26.08, 26.34, 26.96, 29.10, 29.74 and 34.30±0.2° 2θ.

* * * * *